(12) United States Patent
Liang et al.

(10) Patent No.: US 10,005,743 B2
(45) Date of Patent: Jun. 26, 2018

(54) METHODS FOR PRODUCING VILOXAZINE SALTS AND NOVEL POLYMORPHS THEREOF

(71) Applicant: Supernus Pharmaceuticals, Inc., Rockville, MD (US)

(72) Inventors: Likan Liang, Boyds, MD (US); Padmanabh P. Bhatt, Rockville, MD (US); David Dain, Baltimore, MD (US); Jean-Philippe Taquet, Lugrin (FR); Aleksandr Pechenov, Germantown, WI (US); Alexei Tchesnokov, Germantown, WI (US); Reynold Mariaux, Vionnaz (CH)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days. days.

(21) Appl. No.: 15/192,098

(22) Filed: Jun. 24, 2016

(65) Prior Publication Data
US 2016/0304475 A1    Oct. 20, 2016

Related U.S. Application Data

(63) Continuation of application No. 13/084,612, filed on Apr. 12, 2011, now Pat. No. 9,403,783.

(60) Provisional application No. 61/323,151, filed on Apr. 12, 2010.

(51) Int. Cl.
| | |
|---|---|
| *C07D 265/30* | (2006.01) |
| *C07D 265/32* | (2006.01) |
| *C07C 215/08* | (2006.01) |
| *C07C 217/34* | (2006.01) |

(52) U.S. Cl.
CPC .......... *C07D 265/30* (2013.01); *C07C 215/08* (2013.01); *C07C 217/34* (2013.01); *C07D 265/32* (2013.01)

(58) Field of Classification Search
CPC .. C07D 265/30; C07D 265/32; C07C 215/08; C07C 217/34
See application file for complete search history.

(56) References Cited

U.S. PATENT DOCUMENTS

| | | | |
|---|---|---|---|
| 3,712,890 A | 1/1973 | Lee et al. | |
| 3,714,161 A | 1/1973 | Mallion et al. | |
| 3,857,839 A * | 12/1974 | Lee ..................... | C07D 265/30 544/148 |
| 7,326,790 B2 | 2/2008 | Singh et al. | |
| 8,148,525 B2 | 4/2012 | Singh et al. | |
| 9,403,783 B2 * | 8/2016 | Liang ..................... | C07C 217/34 |
| 2003/0040436 A1 | 2/2003 | Emerson et al. | |
| 2003/0105138 A1 | 6/2003 | Lukas-Laskey et al. | |
| 2006/0118002 A1 | 6/2006 | Steinmetz et al. | |
| 2007/0167623 A1 * | 7/2007 | Aulombard ........... | C07C 33/483 544/172 |
| 2010/0240696 A1 | 9/2010 | Mazurov et al. | |
| 2011/0166237 A1 | 7/2011 | Haldavanekar et al. | |
| 2012/0190551 A1 | 7/2012 | Yerkes et al. | |
| 2014/0179568 A1 | 6/2014 | Taylor | |

FOREIGN PATENT DOCUMENTS

| | | |
|---|---|---|
| EP | 0092945 A2 | 11/1983 |
| JP | 50-016795 B1 | 6/1975 |
| JP | 2000-327630 A | 11/2000 |
| JP | 2005-112818 A | 4/2005 |
| JP | 2009-519905 A | 5/2009 |
| JP | 2009-537462 A | 10/2009 |
| WO | WO-98/41497 A1 | 9/1998 |
| WO | WO 2007/030366 A1 | 3/2007 |
| WO | WO 2008/047388 A2 | 4/2008 |
| WO | WO 2011/130194 A2 | 10/2011 |

OTHER PUBLICATIONS

Reexamination Report issued in co-pending Japanese Application No. 2013-505028 dated Aug. 9, 2016.
Wuts, P.G.M., "The Role of Protective Groups in Organic Synthesis," in Greene's Protective Groups in Organic Synthesis, 5th Ed., New Jersey: Wiley, 2014, Chapter 1, p. 1.
Harding et al., "Enantioselective synthesis of (2R,3R)-and (2S,3S)-2-[(3-chlorophenyl)-)2-methoxyphenoxy)methyl]morpholine," Tetrahedron: Asymmetry, 2005, 16:2249-2256.
Weber et al., "Synthesis of Ethers," Phase Transfer Catalysis in Organic Synthesis, vol. 4, Reactivity and Structure Concepts in Organic Chemistry, Hafter et al., eds., (New York, Springer-Verlag, 1977), 85-86.
Audouze et al., "New Series of Morpholine and 1,4-Oxazepane Derivatives as Dopamine D 4 Receptor Ligands: Synthesis and 3D-QSAR Model," J. Med. Chem., 2004, 47:3089-3104, American Chemical Society, XP002430838.
Howe et al., "Optical Isomers of 2-(2-ethyoxyphenoxymethyl)tetrahydro-1,4-oxazine(volixazine) and related compounds," Journal of Medicinal Chemistry, 1976, 19:1074-1076.
Myers et al., "A Solid-Supported, Enantioselective Synthesis Suitable for the Rapid Preparation of Large Numbers of Diverse Structural Analogues of (−)-Saframycin A," Journal of the American Chemistry Society, 2002, 124(44):12969-12971.
Jinbo et al., "Synthesis and Antibacterial Activity of Thiazolopyrazine-Incorporated Tetracyclic Quinolone Antibacterial Agents. 2," Journal of Medicinal Chemistry, 1994, 37(17):2791-2796.
Firestone et al., "Selective delivery of cytotoxic compounds to cells by the LDL pathway," Journal of Medicinal Chemistry, 1984, 27(8):1037-1043.

(Continued)

*Primary Examiner* — Amanda L Aguirre
(74) *Attorney, Agent, or Firm* — Sunit Talapatra; Foley & Lardner LLP

(57) ABSTRACT

Provided here are methods of manufacture of viloxazine and its various salts, as well as viloxazine-related compounds, such as novel intermediate reaction products and polymorphs thereof. In particular, the methods provide a substantially pure API of viloxazine HCl while avoiding undesirable impurities. The methods further provide for separating, identifying, and characterizing novel polymorphs of viloxazine. Further provided are methods for synthesis and identification and characterization of novel intermediates of viloxazine, as well as for some important metabolites and precursors of metabolites of viloxazine.

12 Claims, 9 Drawing Sheets

(56) References Cited

OTHER PUBLICATIONS

Database WPI, Thomson Scientific, London, GB; AN 2004-326476 [34] "New substituted phenoxy propanol amine derivatives, are tyrosinase inhibitors used in skin external preparations as skin-whitening agents," & JP 2005 112818 A (Apr. 25, 2005).
Database Registry, Chemical Abstracts Service, Columbus, Ohio, US; Database accession No. 1215605-65-4, Apr. 2, 2010.
Database Registry, Chemical Abstracts Service, Columbus, Ohio, US, Database accession No. 1049188-99-9, Sep. 14, 2009.
Database Registry, Chemical Abstracts Service, Columbus, Ohio, US, Database accession No. 1183212-94-3, Sep. 13, 2009.
Database Registry, Chemical Abstracts Service, Columbus, Ohio, US, Database accession No. 741245-85-2, Sep. 8, 2004.
Database Registry, Chemical Abstracts Service, Columbus, Ohio, US, Database accession No. 479674-32-3, Jan. 22, 2003.
Database Registry, Chemical Abstracts Service, Columbus, Ohio, US, Database accession No. 439128-99-1, Jul. 17, 2002.
Database CA, Chemistry Abstracts Service, Columbus, Ohio, US; Bairamov, M.R. et al., "Reaction of 2-(p-methoxyphenoxymethyl) oxirane with different amines and amino alcohols," DB accession No. 1980:426024 & UCH. ZAP. AZERB. UN-T. SER. KHIM. N., (1), 69-72, from: Ref. ZH., KHIM. 1980, Abstr. No. 3ZH164, 1979.741245-85-2.
Database PubChem Compound [Online], NCBI; Aug. 16, 2005, "AC1MMDOQ—Compound Summary," Database accession No. CID 3236825.
Ouhabi, J. et al., Acta Crystallographica Section C Crystal Structure Communications, 1990, 46(11):2160-2162.
Serajuddin et al., "Salt formation to improve drug solubility," Advanced Drug Delivery Reviews, Aug. 27, 2007, 59(7):603-616.
Byrn et al., "Pharmaceutical Solids: A Strategic Approach to Regulatory Considerations," Pharmaceutical Research, Kluwer Academic Publishers, 1995, 12(7):945-954.
Blackburn, T.P. et al., "Effects of viloxazine, its optical isomers and its major metabolites on biogenic amine uptake mechanisms in vitro and in vivo," European Journal of Pharmacology, 1978, 52(3-4):367-374.
Soula, G., "Tris(polyoxaalkyl)amines (Trident), a new class of solid-liquid phase-transfer catalysts," Journal of Organic Chemistry, Oct. 4, 1985, 50(20):3717-3721, XP002105964, American Chemical Society, Easton, US, ISSN: 0022-3263, DOI: 10.1021/J000220A009 the whole document.
Liu et al. "A novel method for synthesis of aryl glycidyl ethers", Synthetic Communications, 1994, vol. 24, No. 6, pp. 833-838.
Pchelka et al., "Improvement and simplification of synthesis of 3-aryloxy-a,2-epoxypropanes using solvent-free conditions and microwave irradiations. Relation with medium effects and reaction mechanism", Tetrahedron, 2006, vol. 62, pp. 10968-10979.
Japanese Office Action issued in co-pending Japanese Patent Application No. 2013-505028, dated Mar. 1, 2016.

\* cited by examiner

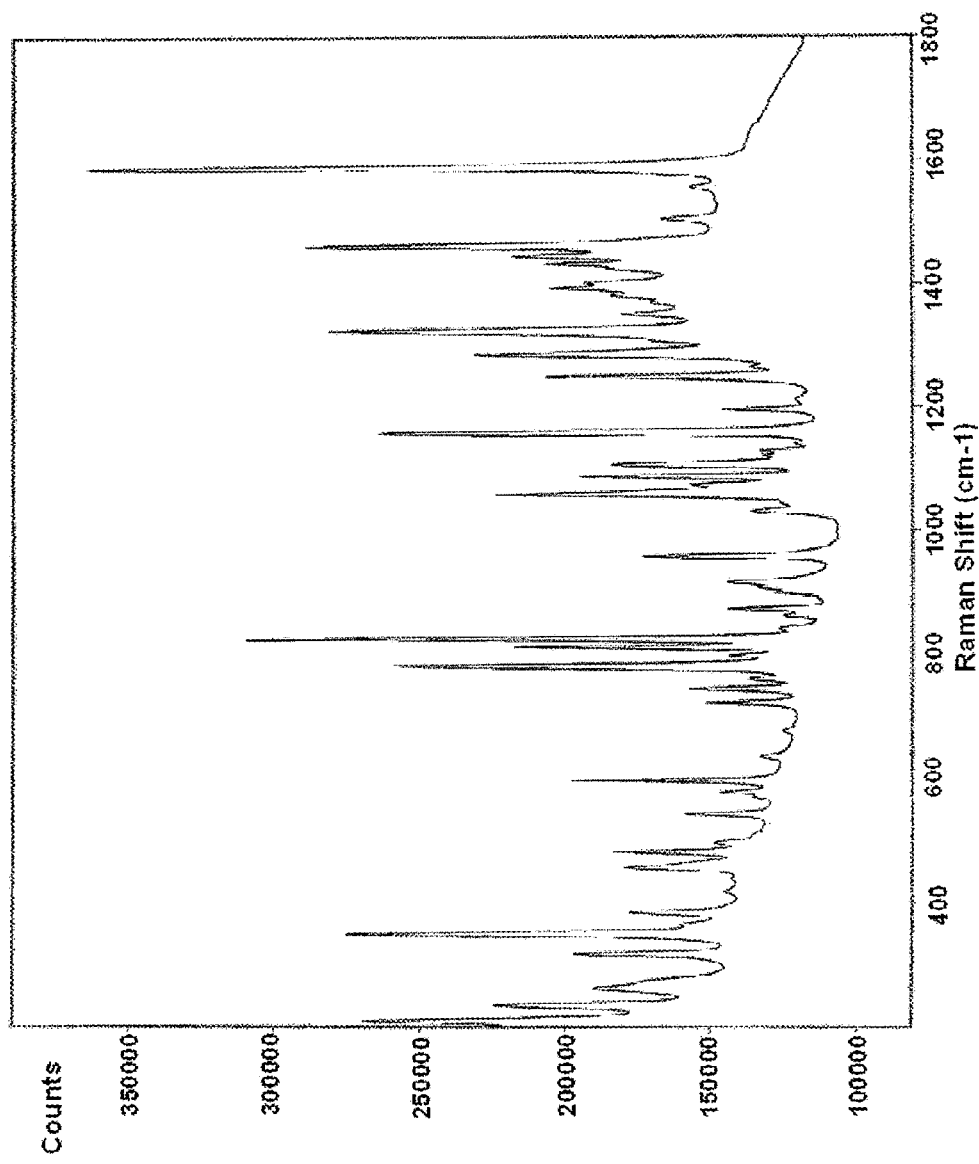

METHODS FOR PRODUCING VILOXAZINE SALTS AND NOVEL POLYMORPHS THEREOF

CROSS-REFERENCE TO RELATED APPLICATIONS

This application is a Continuation Application of U.S. patent application Ser. No. 13/084,612, filed Apr. 12, 2011, which claims priority to the U.S. Provisional Application No. 61/323,151, filed on Apr. 12, 2010, the contents of these applications are incorporated in their entirety.

FIELD

Described herein are methods for improved production of active pharmaceutical ingredients ("APIs") such as viloxazine, including methods having increased yields and producing decreased amounts of impurities. This disclosure further describes and characterizes salts of APIs such as viloxazine hydrochloride, including novel polymorphs thereof.

BACKGROUND

Viloxazine ((R,S)-2-[(2-ethoxyphenoxy)methyl]morpholine]) is a bicyclic morpholine derivative, assigned CAS No. 46817-91-8 (CAS No. 35604-67-2 for the HCl salt). It is characterized by the formula $C_{13}H_{19}NO_3$, with a molecular mass of 237.295 g/mol. Viloxazine has two stereoisomers, (S)-(−)- and (R)-(+)-isomer, which have the following chemical structures:

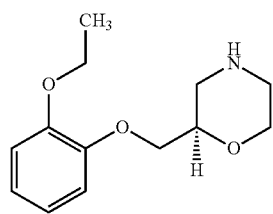

Formula 1

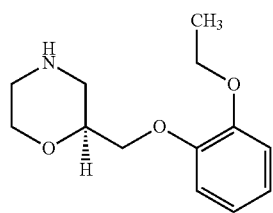

Formula 2

Viloxazine is known to have several desirable pharmacologic uses, including treatment of depression, nocturnal enuresis, narcolepsy, sleep disorders, and alcoholism, among others. In vivo, viloxazine acts as a selective norepinephrine reuptake inhibitor ("NRI"). Between the two stereoisomers, the (S)-(−)-isomer is known to be five times as pharmacologically active as the (R)-(+)-isomer. See, e.g., "Optical Isomers of 2-(2-ethoxyphenoxymethyl)tetrahydro-1,4 oxazine (viloxazine) and Related Compounds" (Journal of Medicinal Chemistry, Jan. 9, 1976, 19(8); 1074) in which it is disclosed that optical isomers of 2-(2-ethoxyphenoxymethyl)tetrahydro-1,4-oxazine (viloxazine) and 2-(3-methoxyphenoxymethyl)tetrahydro-1,4-oxazine were prepared and absolute configurations assigned. The synthesis of optical isomers of viloxazine analogs of known configuration was accomplished by resolution of the intermediate 4-benzyl-2-(p-toluenesulfonyloxymethyl)tetrahydro-1,4-oxazine isomers.

Some unsatisfactory methods of synthesizing viloxazine are known in the art. For example, as disclosed in U.S. Pat. No. 3,714,161, viloxazine is prepared by reacting ethoxyphenol with epichlorohydrin to afford the epoxide intermediate 1-(2-ethoxyphenoxy)-2,3-epoxypropane. This epoxide intermediate is then treated with benzylamine followed with chloroacetyl chloride. The resulting morpholinone is then reduced by lithium aluminum hydride and then by Pd/C-catalyzed hydrogenation to yield viloxazine free base.

Yet another unsatisfactory synthesis of viloxazine is disclosed in U.S. Pat. No. 3,712,890, which describes a process to prepare viloxazine HCl, wherein the epoxide intermediate, 1-(2-ethoxyphenoxy)-2,3-epoxypropane, is reacted with 2-aminoethyl hydrogen sulfate in ethanol in the presence of sodium hydroxide to form viloxazine free base. The product is extracted with diethyl ether from the aqueous solution obtained by evaporating the solvent in the reaction mixture then adding water to the residue. The ethereal extract is dried over a drying agent and the solvent is removed. Viloxazine HCl salt is finally obtained by dissolving the previous residue in isopropanol, concentrated aqueous HCl, and ethyl acetate followed by filtration.

The foregoing methods of synthesizing viloxazine suffer from a number of deficiencies, such as low reaction yield and unacceptably large amount of impurities in the resulting product. Effective elimination or removal of impurities, especially those impurities possessing genotoxicity or other toxicities, is critical to render safe pharmaceutical products. For example, certain reagents traditionally utilized in viloxazine HCl preparation, such as epichlorohydrin and 2-aminoethyl hydrogen sulfate, present a special problem due to their toxicity. There is a need for effective methods to remove or limit harmful impurities down to a level that is appropriate and safe according to contemporary sound medical standards and judgment. Accordingly, a continuing and unmet need exists for new and improved methods of manufacturing viloxazine and its various salts to yield adequate quantities of pharmacologically desirable API with predictable and reliable control of impurities.

Polymorph control is also an important aspect of producing APIs and their associated salts that are used in pharmaceutical products. However, no polymorphs of viloxazine HCl have previously been disclosed. A need therefore exists for new polymorphic forms of viloxazine that have improved pharmacological properties.

SUMMARY OF THE INVENTION

Provided herein are new and improved methods of manufacture of viloxazine and its various salts, as well as viloxazine-related compounds, such as novel intermediate reaction products. In particular, the methods herein provide a substantially pure API of viloxazine HCl while avoiding undesirable impurities. The methods further provide for synthesizing, separating, identifying, and characterizing novel polymorphs of viloxazine. Further provided are methods for synthesis and identification and characterization of novel intermediates of viloxazine, as well as for some important metabolites and precursors of metabolites of viloxazine.

In an exemplary embodiment, the invention provides a substantially pure composition suitable for use as an active pharmaceutical ingredient, the composition consisting essentially of viloxazine or a pharmaceutically acceptable salt thereof and comprising less than about 1.5 μg of any genotoxic impurity per expected human daily dosage. In another exemplary embodiment, the composition comprises less than 0.5 μg of any genotoxic impurity per expected human daily dosage.

In a further embodiment, the invention provides a method of manufacturing viloxazine through a 3-step process, wherein in the first step 2-ethoxyphenol and epichlorhydrin are reacted to produce 1-(2-ethoxyphenoxy)-2,3-epoxypropane (Epoxide 1); in the second step, 1-(2-ethoxyphenoxy)-2,3-epoxypropane (Epoxide 1) is converted into viloxazine base which is further converted into viloxazine salt, and in the third Step viloxazine salt is purified/recrystallized, and various polymorphic forms of viloxazine salt are prepared.

In a further embodiment, the invention provides a method of manufacturing a 2-substituted morpholine, such as viloxazine, comprising (1) providing a diol compound according to the following formula:

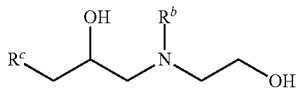

wherein $R^b$ is a hydrogen or a nitrogen-protecting group, and $R^c$ is a substituted or unsubstituted aryloxy group, a substituted or unsubstituted alkyl group, or a substituted or unsubstituted alkoxy group; (2) reacting the diol compound with a base and a cyclization agent to yield a 2-substituted morpholine having the following formula:

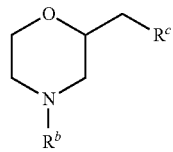

In a variation of step (2) in the embodiment, a single phasic, or a liquid-liquid or solid-liquid biphasic system can be employed. In a further variation of step (2) in the embodiment, a phase transfer catalyst can be employed. In yet another further variation of the embodiment, the diol is treated with a base first, followed by cyclization agent.

In yet another embodiment, the invention provides a compound according to the following formula:

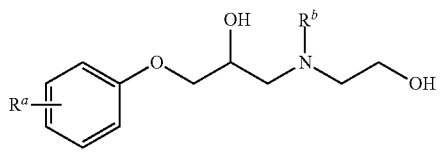

wherein $R^a$ is a substituted or unsubstituted aryloxy group or a substituted or unsubstituted alkoxy group, and $R^b$ is hydrogen or a nitrogen-protecting group.

In yet another embodiment, the invention provides a method of manufacturing viloxazine by reacting 1-(2-ethoxyphenoxy)-2,3-epoxypropane with 2-aminoethyl hydrogen sulfate in a solution with a very large excess of a base. In a further variation of the embodiment, the base is added to the reaction mixture in a stepwise manner.

In yet another embodiment, the invention provides a composition comprising viloxazine hydrochloride polymorph Form A, the polymorph having a powder X-ray diffraction spectrum and a Raman infrared spectrum as illustrated in FIG. 6 and FIG. 9.

In a different embodiment, the invention provides a composition comprising viloxazine hydrochloride polymorph Form B, the polymorph having a powder X-ray diffraction spectrum and a Raman infrared spectrum as illustrated in FIG. 7 and FIG. 10.

In yet another embodiment, the invention provides a pharmaceutical composition comprising viloxazine hydrochloride polymorph Form A, polymorph Form B, or a combination thereof.

Additional features may be understood by referring to the accompanying drawings, which should be read in conjunction with the following detailed description and examples.

BRIEF DESCRIPTION OF THE DRAWINGS

FIG. 10 shows a Raman spectrum of viloxazine HCl, Form B.

DETAILED DESCRIPTION

Provided herein are new and improved methods of manufacture of substantially pure compositions of viloxazine and pharmaceutically acceptable salts and polymorphs thereof with improved control of impurities to thereby provide materials suitable for pharmaceutical applications.

For the sake of convenience and without putting any limitations thereof, the methods of manufacture of viloxazine have been separated into several steps, each step being disclosed herein in a multiplicity of non-limiting embodiments. These steps comprise Step 1, during which 2-ethoxyphenol and epichlorhydrin are reacted to produce 1-(2-ethoxyphenoxy)-2,3-epoxypropane (Epoxide 1); Step 2, during which 1-(2-ethoxyphenoxy)-2,3-epoxypropane (Epoxide 1) is converted into viloxazine base which is further converted into viloxazine salt, and Step 3, during which viloxazine salt is purified/recrystallized, and various polymorphic forms of viloxazine salt are prepared.

The above-mentioned steps will be considered below in more details.

The process of the Step 1 may be advantageously carried out in the presence of a phase-transfer catalyst to afford near quantitative yield of 1-(2-ethoxyphenoxy)-2,3-epoxypropane. Alternatively, the process may make use of a Finkelstein catalyst described in more details below. Additionally, the reaction may take place without the use of the catalyst.

Figure 1:
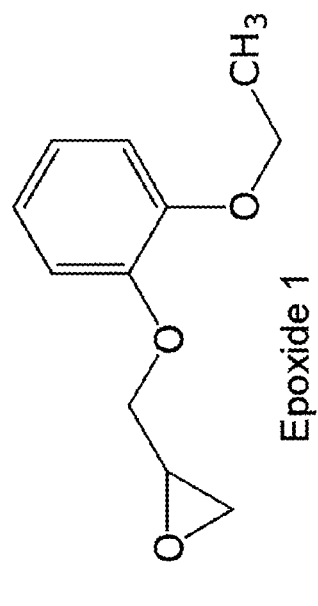
FIG. 1, schematically illustrates the preparation of 1-(2-ethoxyphenoxy)-2,3-epoxypropane ("Epoxide 1") in accordance with the first step ("Step I") of an exemplary synthesis of viloxazine.
Figure 1:
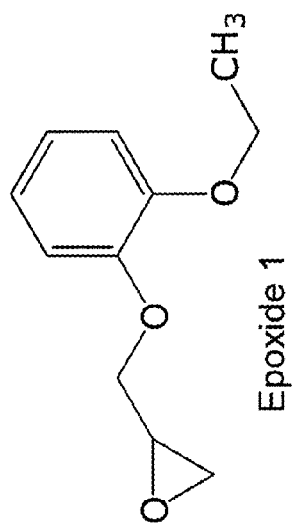

FIG. 1, depicted below, schematically illustrates the preparation of 1-(2-ethoxyphenoxy)-2,3-epoxypropane ("Epoxide 1") in accordance with Step I of an exemplary synthesis of viloxazine:

Step I:

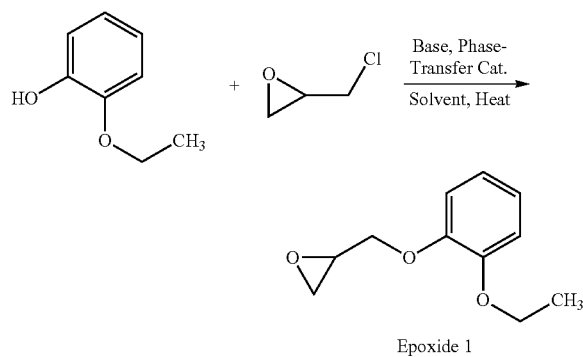

Epoxide 1

In one embodiment of the Step 1, the preparation of 1-(2-ethoxyphenoxy)-2,3-epoxypropane (epoxide 1) can be effected by the use of a phase transfer catalyst in the presence of a solid or liquid base with a solution of a corresponding phenol and epichlorohydrin in one or more solvents (FIG. 1). The phase transfer catalyst can be selected from ammonium salts, such as benzyltriethylammonium salts, benzyltrimethylammonium salts, and tetrabutylammonium salts, phosphonium salts, guanidinium salts, crown ether, polyethylene glycol, polyethylene glycol ether, or polyethylene glycol ester, or other phase transfer catalysts know in the art. The solid or liquid base can be a carbonate such as alkali carbonate, NaOH, KOH, LiOH, LiOH/LiCl, amines such as mono-, di- or tri-substituted amines (such as diethylamine, triethylamine, dibutylamine, tributylamine), DMAP, or other appropriate base. The solvents used in the solution of a corresponding phenol and epichlorohydrin include but are not limited to ethers such as methyl t-butyl ether, ketones, non-substituted or substituted aromatic solvents (xylene), halo-substituted hydrocarbons (e.g. CH2Cl2, CHCl3), THF, DMF, dioxanes, non-substituted and substituted pyridines, acetonitrile, pyrrolidones, nitromethane, or other appropriate solvent. Additional catalyst, such as, for example, Finkelstein catalyst, can also be used in the process of this embodiment. This reaction preferably takes place at an elevated temperature. In one variation of the embodiment, the temperature is above 50° C. In another variation, epichlorohydrin, potassium carbonate, and a phase transfer catalyst are mixed with a solution of 2-ethoxyphenol in a solvent at an elevated temperature, such as 50-60° C. After the reaction is complete, the reaction mixture can be washed with water, followed by work-up procedures known in the art. Variations of this embodiment of the invention are further disclosed in Examples 1-8.

In one variation of the above embodiment of the Step 1, Epoxide 1 is prepared by reacting 2-ethoxyphenol and epichlorohydrin in a solvent in the presence of two different catalysts, and a base in a solid state. The first catalyst is a phase transfer catalyst as described above; the second catalyst is a Finkelstein reaction catalyst. Without putting any limitation hereon, metal iodide and metal bromide salts, such as potassium iodide, may be used as an example of a Finkelstein catalyst. The phase transfer catalyst and a solvent may be selected from any phase transfer catalysts and solvents known in the art. Potassium carbonate may be used as a non-limiting example of a solid base. Using the solid base in a powdered form may be highly beneficial due to the greatly enhanced interface and limiting the side reactions. This variation of the embodiment is further illustrated by Example 9. In another variation of the embodiment, liquid base such as triethylamine can be used to replace the solid base.

In a different embodiment of Step 1, 2-ethoxyphenol and epichlorohydrin are reacted in a solvent-free system that comprises a solid or liquid base, a phase transfer catalyst as listed above and a Finkelstein catalyst.

Figure 2:
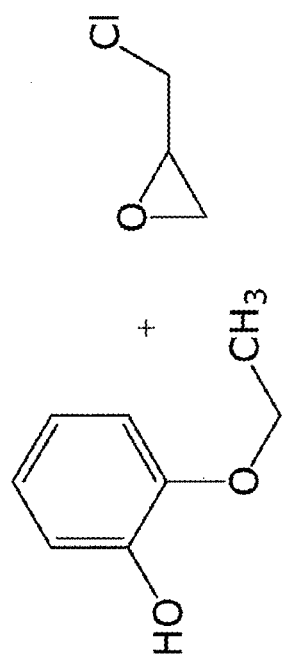
FIG. 2, schematically illustrates the preparation of 1-(2-ethoxyphenoxy)-2,3-epoxypropane ("Epoxide 1") in accordance with the first step ("Step I") of another exemplary synthesis of viloxazine (biphasic)
Figure 2:
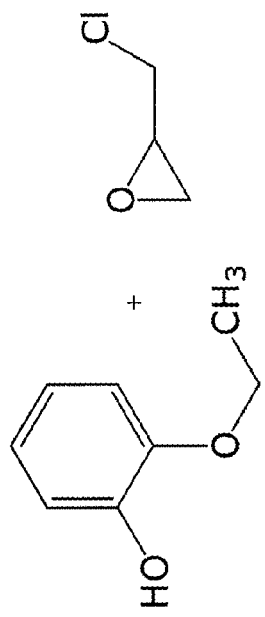

FIG. 2, depicted below, schematically illustrates the preparation of 1-(2-ethoxyphenoxy)-2,3-epoxypropane ("Epoxide 1") in accordance with the Step I of another exemplary synthesis of viloxazine (biphasic):

Step I (Alternative Embodiment):

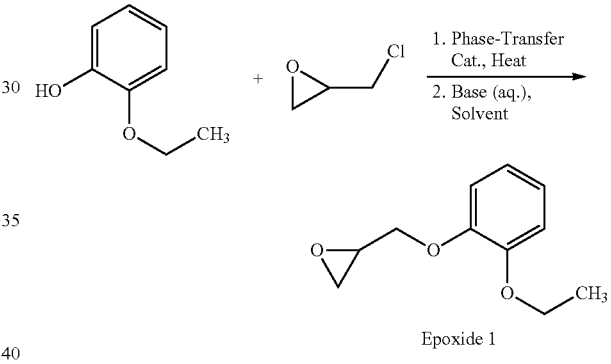

Epoxide 1

In this embodiment of Step 1, illustrated in FIG. 2, Epoxide 1 can be prepared by reacting epichlorohydrin with 2-ethoxyphenol in the presence of a catalytic amount of a phase transfer catalyst without the use of solvents at elevated temperatures in a two-stage process to afford near quantitative yield of 1-(2-ethoxyphenoxy)-2,3-epoxypropane with very few side products. This embodiment of the invention is further illustrated by a non-limiting Example 12. The phase transfer catalyst for this embodiment can be selected from ammonium salts such as benzyltriethylammonium salts, benzyltrimethylammonium salts, tetrabutylammonium salts, etc; phosphonium salts, guanidinium salts, crown ether, polyethylene glycol, polyethylene glycol ether, or polyethylene glycol ester, or other phase transfer catalysts know in the art. The first stage of the process of this embodiment may take place without a solvent in a presence of a large excess of epichlorohydrin. This stage is followed by a de-chlorination stage, before or after removal of excess epichlorohydrin, using a base and a solvent. The reaction produces 1-(2-ethoxyphenoxy)-2,3-epoxypropane in high yield. Example of the bases used herein include but are not limited to NaOH, KOH, LiOH, LiOH/LiCl, K2CO3, Na2CO3, amines such as mono-, di- or tri-substituted amines (such as diethylamine, triethylamine, dibutylamine, tributylamine etc.), DMAP. In one variation of this embodiment of Step 1, the phase transfer catalyst may be used only at the de-chlorination stage of the process. The de-chlorination stage can be carried out in a biphasic system or in a single phase system. For a biphasic system, it can be an organic-aqueous liquid biphasic system, or a liquid-solid biphasic system. Solvents that are useful for the process include but are not limited to non-substituted and substituted aromatic solvents (e.g. toluene, benzene, chlorobenzene, dimethylbenzene, xylene), halo-substituted hydrocarbons (e.g. CH2Cl2, CHCl3), THF, dioxanes, DMF, DMSO, non-substituted and substituted pyridines, ketones, pyrrolidones, ethers, acetonitrile, nitromethane. As mentioned above, this process takes place at the elevated temperature. In one variation of the embodiment, the temperature is above 60° C. In another variation, 2-ethoxyphenol and epichlorohydrin are heated to 60-90° C. for a period of time in the presence of phase transfer catalyst. Excess of epichlorohydrin is removed and the residue is dissolved in a solvent such as toluene or benzene treated with an aqueous base solution, such as NaOH, KOH, LiOH, LiOH/LiCl. In yet another variation of the embodiment, the residue after epichlorohydrin removal can be dissolved in one or more of the said solvent and treated with a base (solid or liquid but not an aqueous solution) and optionally a second phase transfer catalyst, optionally at elevated temperatures.

In yet another embodiment of Step 1, Epoxide 1 can also be prepared by using a catalyst for a so-called Finkelstein reaction in the presence of a Finkelstein catalyst but without the need to use a phase transfer catalyst. Finkelstein catalysts useful herein include metal iodide salts and metal bromide salts, among others. In one variation of this embodiment, 2-ethoxyphenol and epichlorohydrin are dissolved in a polar aprotic solvent such as DMF, and a catalytic amount of an iodide such as potassium iodide and a base, as solid or liquid, are used. Preferably, the base is used as a solid, such as potassium carbonate powder. This embodiment is further illustrated by the Example 11.

In the alternative embodiment of Step 1, Epoxide 1 can also be prepared by a different method that comprises reacting epichlorohydrin and the corresponding phenol in the presence of a base at a temperature lower than the ambient temperature, especially when a base solution is used, and without the use of a phase transfer catalyst. This embodiment is illustrated by the Example 10.

A very high, almost quantitative, yield of 1-(2-ethoxyphenoxy)-2,3-epoxypropane can be obtained through realizing the above-described embodiments of Step 1, with less impurities generated in Epoxide 1.

Epoxide 1, produced in Step 1 as described above, is used to prepare viloxazine base (viloxazine), which is further converted into viloxazine salt through the processes of Step 2.

Figure 3:
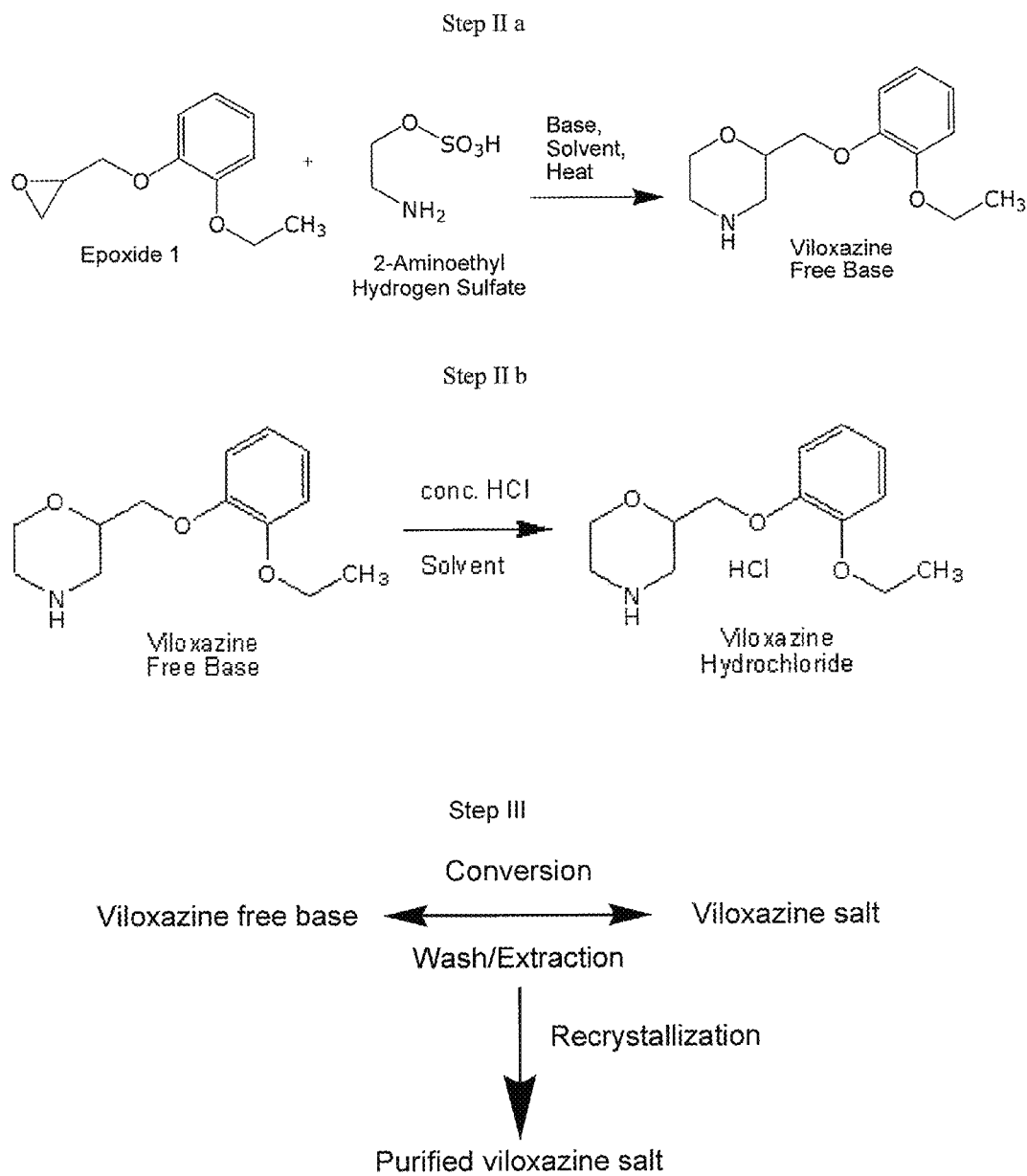
FIG. 3, schematically illustrates the preparation of viloxazine ("Step IIa") and the preparation of viloxazine hydrochloride ("Step IIb"), as well as their purification ("Step III") in accordance with another example embodiment hereof.

FIG. 3, depicted below, schematically illustrates the preparation of viloxazine ("Step IIa") and the preparation of viloxazine hydrochloride ("Step IIb"), as well as their purification ("Step III") in accordance with another example embodiment hereof:

Step IIa:

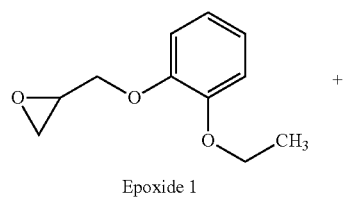

Epoxide 1

+

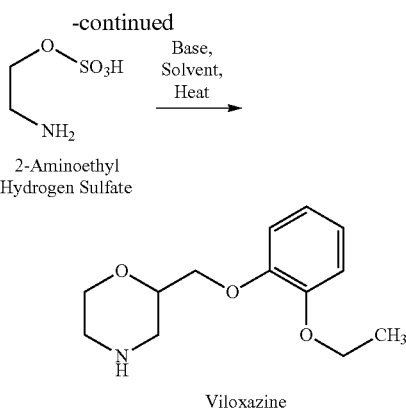

2-Aminoethyl
Hydrogen Sulfate

Viloxazine
Free Base

Step IIb:

Viloxazine
Free Base

Viloxazine
Hydrochloride

Step III:

Viloxazine free base ⇌ (Conversion / Wash/Extraction) Viloxazine salt

↓ Recrystallization

Purified viloxazine salt

In the embodiment of Step 2, illustrated in FIG. 3, the preparation of viloxazine base is achieved by reacting the Epoxide 1 intermediate prepared in Step 1 and aminoethyl hydrogen sulfate in presence of a large excess of a base as illustrated by the Examples 5-7 and 14. The base may be present as a solid or in a solution. Preferably, the molar ratio of the base to Epoxide 1 is more than 10. More preferably the ratio is more than 12. Even more preferably, the ratio is between 15 and 40. It was unexpectedly discovered that the use of a higher ratio of a base results in a faster reaction, less impurities, and lower reaction temperature.

Further advantages may be offered by a specific variation of this embodiment, wherein the base is added to the reaction mixture in several separate steps. For example, a third of the base is added to the reaction mixture, and the mixture is stirred for a period of time. Then the rest of the base is added followed by additional stirring. Alternatively, half of the base is added initially followed by the second half after some period of time, or the base is added in three different parts separated by periods of time. The bases used herein include but are not limited to NaOH, KOH, LiOH, LiOH/LiCl, K2CO3, Na2CO3, amines such as mono-, di- or tri-substituted amines (such as diethylamine, triethylamine, dibutylamine, tributylamine), DMAP, and combinations thereof. In one embodiment of the invention, the base is KOH. In another embodiment, the base is NaOH. In a further embodiment, the base is K2CO3 powder. In yet further embodiment, the base is triethylamine. This embodiment is illustrated further by Examples 13, 15 and 16.

In another exemplary embodiment of Step 2, viloxazine is produced by cyclization of novel intermediate compound "Diol 1," which is made from Epoxide 1 and N-benzyl-aminoethanol. This method allows one to drastically reduce the use of potentially toxic materials in the manufacturing process, completely eliminating some of them such as aminoethyl hydrogen sulfate. The first stage of the reaction results in the formation of an intermediate of Formula 3 (Diol 1), which is a new, previously unidentified compound.

Formula 3

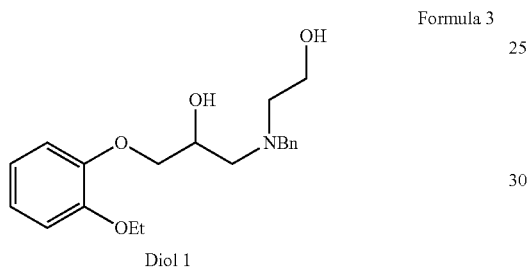

Diol 1

Figure 4:
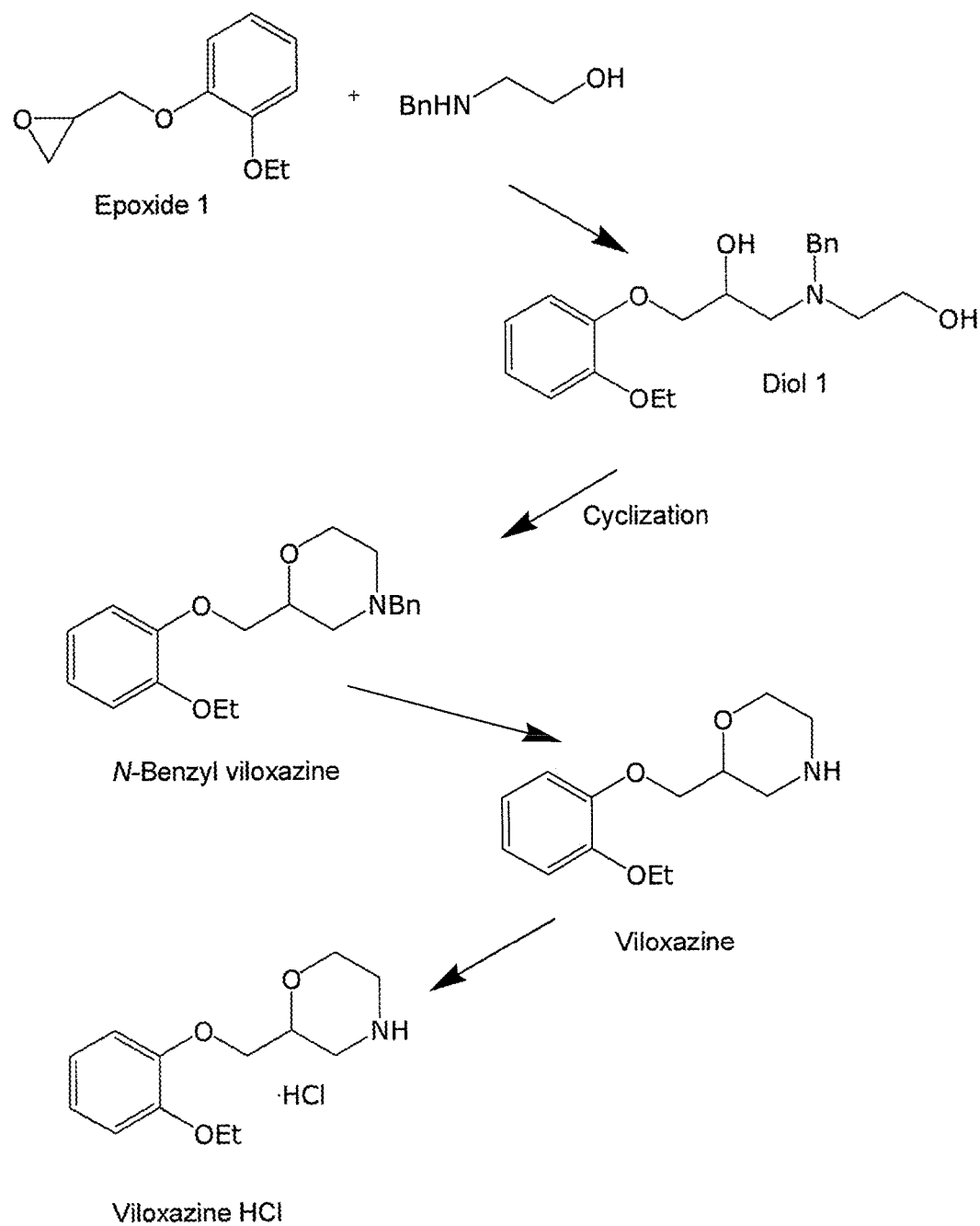
FIG. 4, schematically illustrates the preparation of viloxazine and its salts via "Diol 1" in accordance with another exemplary embodiment hereof (Bn=benzyl, Et=ethyl).

FIG. 4, depicted below, schematically illustrates the preparation of viloxazine and its salts via "Diol 1" in accordance with another exemplary embodiment hereof (Bn=benzyl, Et=ethyl):

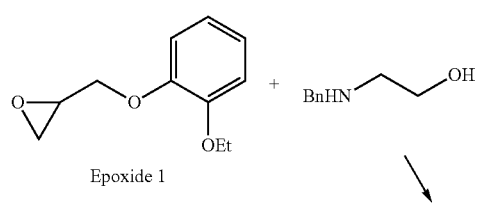

Epoxide 1

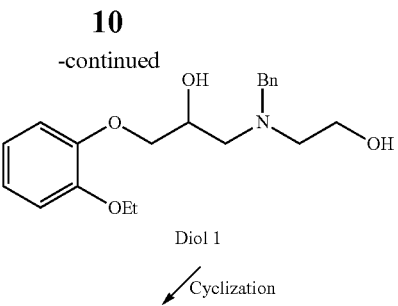

Diol 1

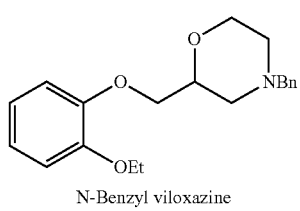

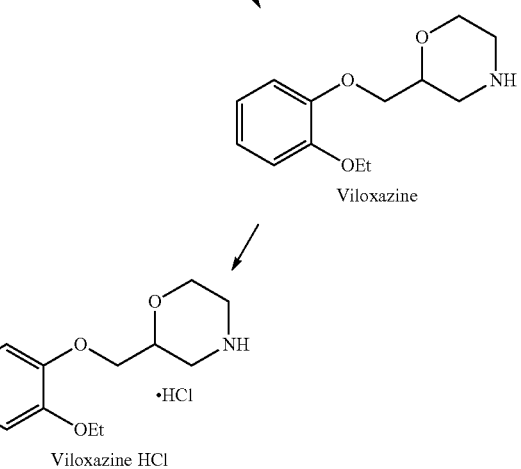

Figure 5:
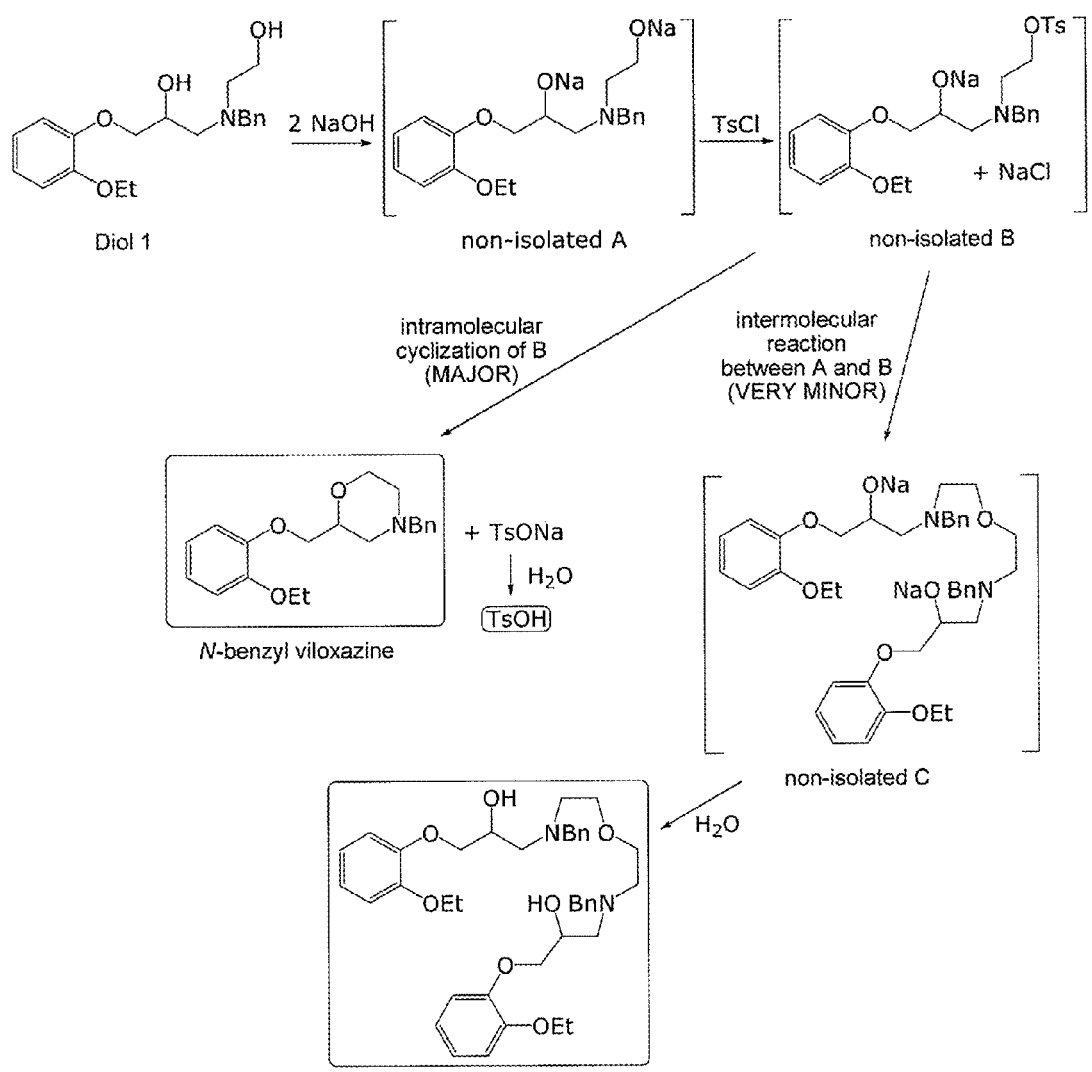
FIG. 5, schematically illustrates the cyclization of Diol 1, as well as some side-reactions thereof.

As illustrated in FIG. 4, Diol 1 is turned into N-benzyl viloxazine by cyclization. Removal of the benzyl protective group yields viloxazine base. Similarly, FIG. 5, depicted below, schematically illustrates the cyclization of Diol 1, as well as some side-reactions thereof.

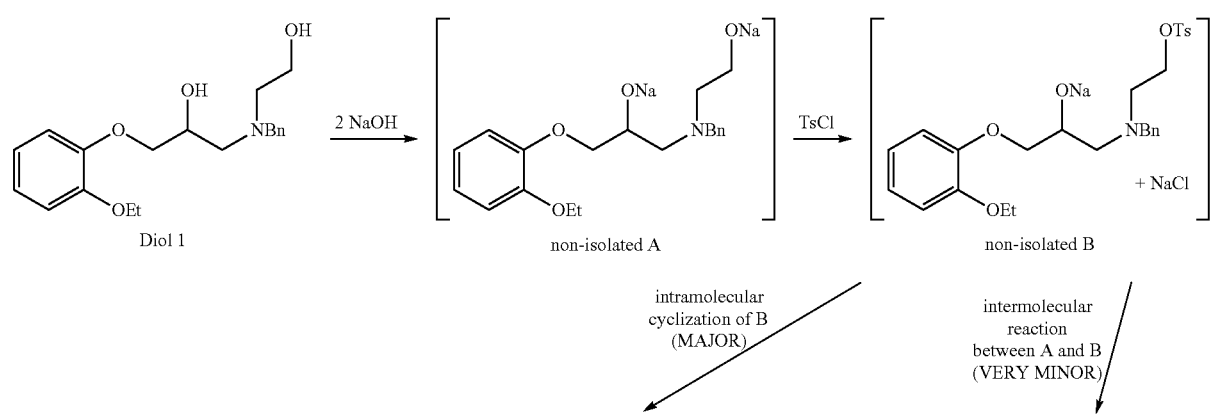

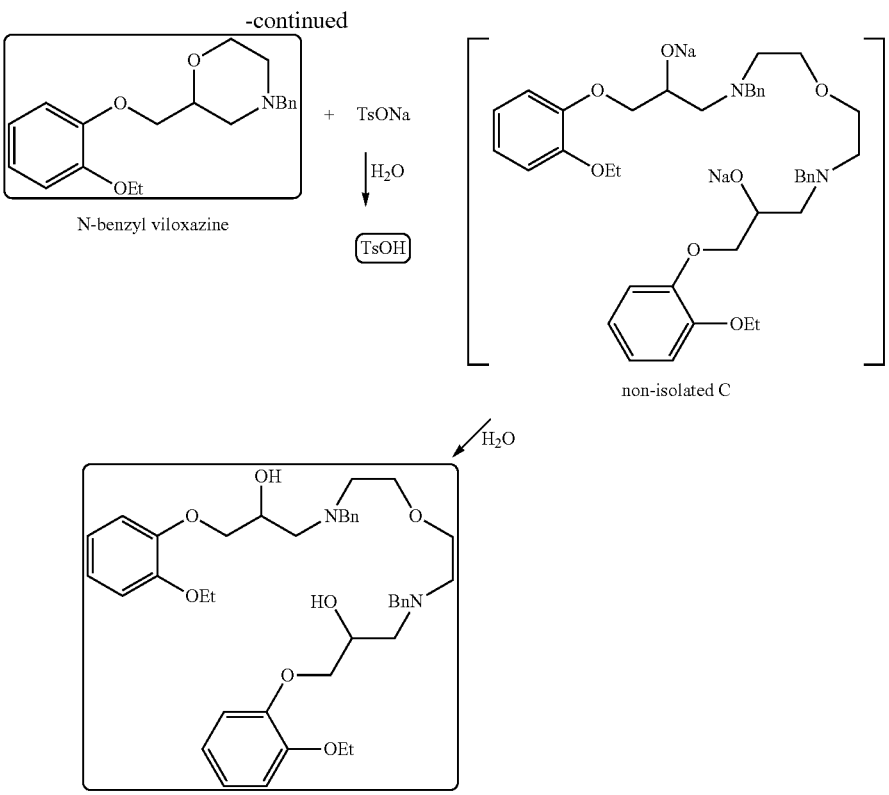

In one variation of the embodiment, epoxide 1 and N-benzyl aminoethanol can be refluxed in a solvent to form Diol 1 in quantitative yield. The solvent is selected from those having a boiling point of 50° C. or more. Preferably, the boiling point is 60° C. or more. More preferably, the boiling point is 70° C. or more. For example, Diol 1 can be prepared in quantitative yield by refluxing toluene with 2-4 volume/g of the epoxide 1 and about 1 equivalent of N-benzyl aminoethanol, which can be added slowly to the solution at about 110° C. (see Example 17).

Any of several methods can be used to efficiently perform the cyclization reaction of Diol 1. In one example, Diol 1 can be turned into N-benzyl viloxazine via cyclization reaction effected by an acid, such as sulfuric acid or hydrochloric acid.

In another variation of the embodiment, cyclization can be achieved through the use of a cyclization agent. Examples of the cyclization agents include but are not limited to sulfonyl halides such as tosyl chloride, brosyl chloride, nosyl chloride and mesyl chloride, DMSO, alumina. Other methods for cyclization of diols known in the art can also be used. The cyclization can be carried out in a biphasic system or a single phase system.

Further, it was unexpectedly discovered that a phase transfer catalyst can also be advantageously utilized in the cyclization. The phase transfer catalyst used herein can be selected from ammonium salts, phosphonium salts, guanidinium salts, crown ether, polyethylene glycol, polyethylene glycol ether, or polyethylene glycol ester, or other phase transfer catalysts known in the art.

Bases can be used to facilitate the cyclization reaction, especially when the cyclization agent is a sulfonyl chloride. The bases that are useful in the said process include but are not limited to NaOH, KOH, LiOH, LiOH/LiCl, $K_2CO_3$, $Na_2CO_3$, nitrogen-containing bases such as mono-, di- or tri-substituted amines (such as diethylamine, triethylamine, dibutylamine, tributylamine), dimethylaminopyridine (DMAP), N,N-diisopropylethylamine (DIPEA), 1,4-diazabicyclo[2.2.2]octane (DABCO), 1,8-diazabicyclo[5.4.0]undec-7-ene (DBU), piperidine and derivatives, pyrrolidine and derivatives, quinine, imidazole, alkali salts of carbanions, amides, and hydrides.

Solvents can also be used to facilitate the cyclization reaction. Examples of the solvents used herein include, but are not limited to, non-substituted and substituted aromatic solvents (e.g. toluene, benzene, chlorobenzene, dimethylbenzene, xylene), halo-substituted hydrocarbons (e.g. $CH_2Cl_2$, $CHCl_3$), THF, dioxanes, tetrahydrofuran (THF), N,N-dimethylformamide (DMF), dimethyl sulfoxide (DMSO), non-substituted and substituted pyridines, ketones, pyrrolidones, ethers, acetonitrile, nitromethane. Water can also be used, especially in a biphasic system. In one variation of this embodiment, cyclization can be carried out in the presence of a phase transfer catalyst in a biphasic system wherein Diol 1 is dissolved in the organic phase and the base is dissolved in the aqueous phase. For example, Diol 1 is treated with toluenesulfonyl chloride in the presence of phase transfer catalyst benzyltriethylammonium chloride in a biphasic system wherein an aqueous solution of NaOH is used together with an organic solvent such as toluene. In a separate variation of this embodiment, a solid base may be successfully used in this step instead of an aqueous base in a solid-liquid biphasic system.

In a further embodiment, the invention provides a method of manufacturing a 2-substituted morpholine, such as viloxazine, comprising (1) providing a diol compound according to the following formula:

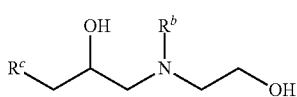

wherein $R^b$ is a hydrogen or a nitrogen-protecting group, and $R^c$ is a substituted or unsubstituted aryloxy group, a substituted or unsubstituted alkyl group, or a substituted or unsubstituted alkoxy group; (2) reacting the diol compound with a base and a cyclization agent to yield a 2-substituted morpholine having the following formula:

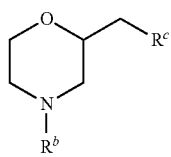

In a variation of step 2 of the embodiment, a single-phasic, or a liquid-liquid or solid-liquid biphasic system can be employed. In a further variation of step 2 in the embodiment, a phase transfer catalyst can be employed. In yet another further variation of the embodiment, the diol is treated with a base first, followed by a cyclization agent.

The addition sequence and the ratio of the reagents for the cyclization reaction can be controlled to obtain maximum yield, improve the purity of the product or to control the side reactions that lead to the formation of two minor, but previously uncharacterized, impurities of Formula 4 and Formula 5:

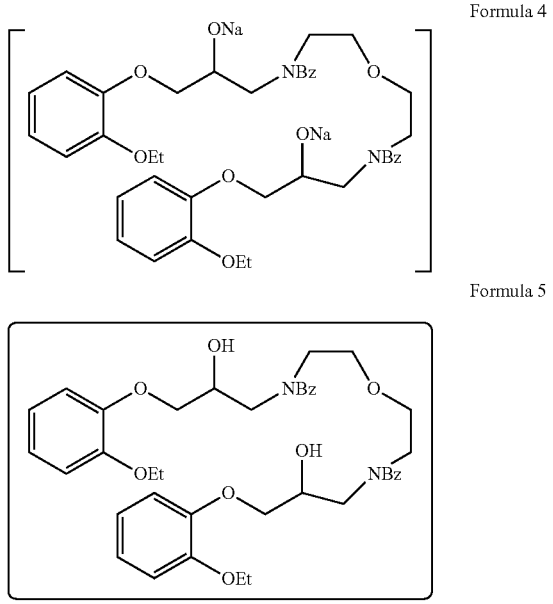

For example, the cyclization agent may be added to the mix after the base is introduced. The Diol 1 concentration may be controlled to prevent the formation of the by-products.

This embodiment of step 2 and its variations are further illustrated in Example 17.

Still referring to FIG. 4, viloxazine can be prepared from N-benzyl viloxazine by removing the benzyl protection group. Many methods can be used to remove the benzyl group herein. Reductive deprotection is one of the methods that can be utilized. Catalytic hydrogenation for removing the benzyl group can be carried out by using Pd/C, Pd (OH)$_2$/C, Pd/CPS (CPS carbon powder support type 1, 2, 3 or 4), and other suitable catalysts know in the art. Hydrogen source can be from H2, or in situ generated hydrogen source such as formamide. Other reagents that can facilitate catalytic debenzylation can also be used. Such facilitating agents can be an agent that reduces catalyst poisoning, such as an acid (see, for example, Example 18).

Known processes for synthesis of viloxazine produce impurities, which can have undesirable pharmacological properties. In particular, known processes provide the following undesirable impurities or by-products: (1) Epichlorohydrin and/or 1-(2-ethoxyphenoxy)-2,3-epoxypropane; (2) 2-aminoethyl hydrogen sulfate; and (3) aminoethyl sulfate ester of an alcohol. These undesirable by-products can be eliminated, or their amounts can be drastically reduced, by the improved methods of synthesis of viloxazine as described above. The removal of the remaining impurities, especially those having higher toxicity potential, can be accomplished by the improved techniques for the isolation and purification of the reaction products. These techniques include free base-salt interconversion that may be performed in multiple cycles; extraction step during work-up and/or during base-salt interconversion; additional crystallization, precipitation, washing, or drying step performed during one or more cycles of free base-salt conversion; one or more cycles of recrystallization, or combinations of the above techniques.

In a further reference to Step 2, some embodiments of the current method as described above avoid the use of toxic compounds like 2-aminoethyl hydrogen sulfate, thus completely eliminating their presence in the final product.

Referring to the embodiments of Step 2, after viloxazine free base is formed, it can be extracted into a solvent such as methyl tert-butyl ether, and then converted to HCl salt by using an aqueous HCl solution. The crude viloxazine HCl can be purified by 1. conversion to viloxazine free base by using a base solution; 2. extraction by a solvent such as methyl tert-butyl ether, 3. optionally washing or drying or filtering the extraction solution, and 4. converting the free base to the salt by using an aqueous HCl solution. This cycle may be repeated as necessary until the desired purity is achieved. Once the conversion cycle is complete, the free base can be turned into the HCl salt by using HCl and a solvent system suitable for preparing a particular polymorph of viloxazine HCl. Alternatively, the viloxazine HCl salt can undergo one or more cycles of recrystallization using a suitable solvent system to produce a desired polymorph of viloxazine HCl. Analytical methods capable of detecting extremely low threshold levels set for genotoxic compounds by today's standards show that viloxazine HCl product thus produced has virtually no trace of the epichlorohydrin, 1-(2-ethoxyphenoxy)-2,3-epoxypropane, and 2-aminoethyl hydrogen sulfate (even if this reagent was used in the reaction).

In one embodiment, the methods provide viloxazine and its HCl salt with amounts of less than about 2.5 ppm of impurities selected from the group consisting of epichlorohydrin, 1-(2-ethoxyphenoxy)-2,3-epoxypropane, and 2-aminoethyl hydrogen sulfate. It is important to note that no alcohol esters of aminoethyl sulfate, which are potentially toxic materials, are formed through the processes of the current invention.

In another embodiment, the methods provide viloxazine and its HCl salt with detectable amounts of less than about 1 ppm of impurities selected from the group consisting of epichlorohydrin, 1-(2-ethoxyphenoxy)-2,3-epoxypropane, and 2-aminoethyl hydrogen sulfate.

In a further embodiment, the methods herein provide viloxazine and its HCl salt with no detectable amounts of impurities selected from the group consisting of epichlorohydrin, 1-(2-ethoxyphenoxy)-2,3-epoxypropane, and 2-aminoethyl hydrogen sulfate (see Example 22).

In a further embodiment, the methods herein provide viloxazine and its HCl salt completely free of 2-aminoethyl hydrogen sulfate.

The invention therefore provides a substantially pure composition consisting essentially of viloxazine or a pharmaceutically acceptable salt thereof. The term "substantially pure" refers to compositions containing essentially only the active pharmaceutical ingredient and less than about 1.5 µg (or preferably less than about 0.5 µg) of any genotoxic impurity per expected human daily dosage, and they are therefore suitable for use in the preparation of pharmaceutical dosage forms intended for human consumption. Further, the term "substantially pure" refers to compositions containing at least about 99% (or more preferably at least about 99.5%, or even more preferably at least about 99.9% to about 99.99%) by weight of the active pharmaceutical ingredient. Even further, the term "substantially pure" refers to compositions containing less than about 2.5 ppm (or more preferably less than about 1.5 ppm, or even more preferably less than about 1 ppm) of any impurity. In this context, an "impurity" refers to reaction side-products or residual reagents or undesirable products thereof, which may remain in the active pharmaceutical ingredient after synthesis. Also, the "substantially pure" compositions referred to herein preferably contain only the active pharmaceutical ingredients as the principal or the sole physiologically or pharmacologically active component.

As used herein, the term "genotoxic" refers to compounds or substances that are suspected to, or have demonstrated to, induce genetic mutations, chromosomal breaks and/or chromosomal rearrangements, which can result in cancer.

A typical dosage of viloxazine, provided in the dosage formulation as the hydrochloride salt, is about 1 mg to about 1000 mg per day, e.g., about 50 mg to about 750 mg per day, alternatively, about 100 mg to about 600 mg per day, or alternatively about 150 mg to about 300 mg per day.

By way of example, a "substantially pure" composition of viloxazine (or a pharmaceutically acceptable salt thereof) contains less than about 2.5 ppm epichlorohydrin, less than about 2.5 ppm 1-(2-ethoxy-phenoxy)-2,3 epoxypropane, and less than about 5 ppm of 1-aminoethyl hydrogen sulfate per daily dosage. By way of further example, a "substantially pure" composition of viloxazine (or a pharmaceutically acceptable salt thereof) contains less than about 0.8 ppm of epichlorohydrin, less than about 0.2 ppm of 1-(2-ethoxyphenoxy)-2,3 epoxypropane, and less than about 1.7 ppm of 2-aminoethyl hydrogen sulfate per daily dosage. As mentioned above, alcohol esters of 2-aminoethyl hydrogen sulfate are not being formed in any embodiments of the present invention.

In another important aspect, the current invention is directed towards the unexpected discovery by the inventors of the previously unidentified polymorphic forms of viloxazine salts, such as HCl salt. Previously unknown polymorphs of viloxazine were separated through series of single and multi-solvent crystallizations using fast and slow cooling procedures as well as slurry experiments in water and various organic solvents. Various forms of viloxazine HCl were also prepared by controlling the process or conditions, such as addition sequence of solvents, speed of HCl salt formation, temperature, agitation, time, and other variables. New polymorphs were characterized through XRPD, DSC, TGA, IC, Raman, optical microscopy, $^1$H NMR and moisture sorption analysis.

In one embodiment of the invention, unique crystalline forms of viloxazine were separated through the single-solvent crystallization in the solvent selected from water, acetic acid, methanol (MeOH), ethanol (EtOH), dimethylformamide (DMF), and N-methylpyrrolidone (NMP).

Figure 6:
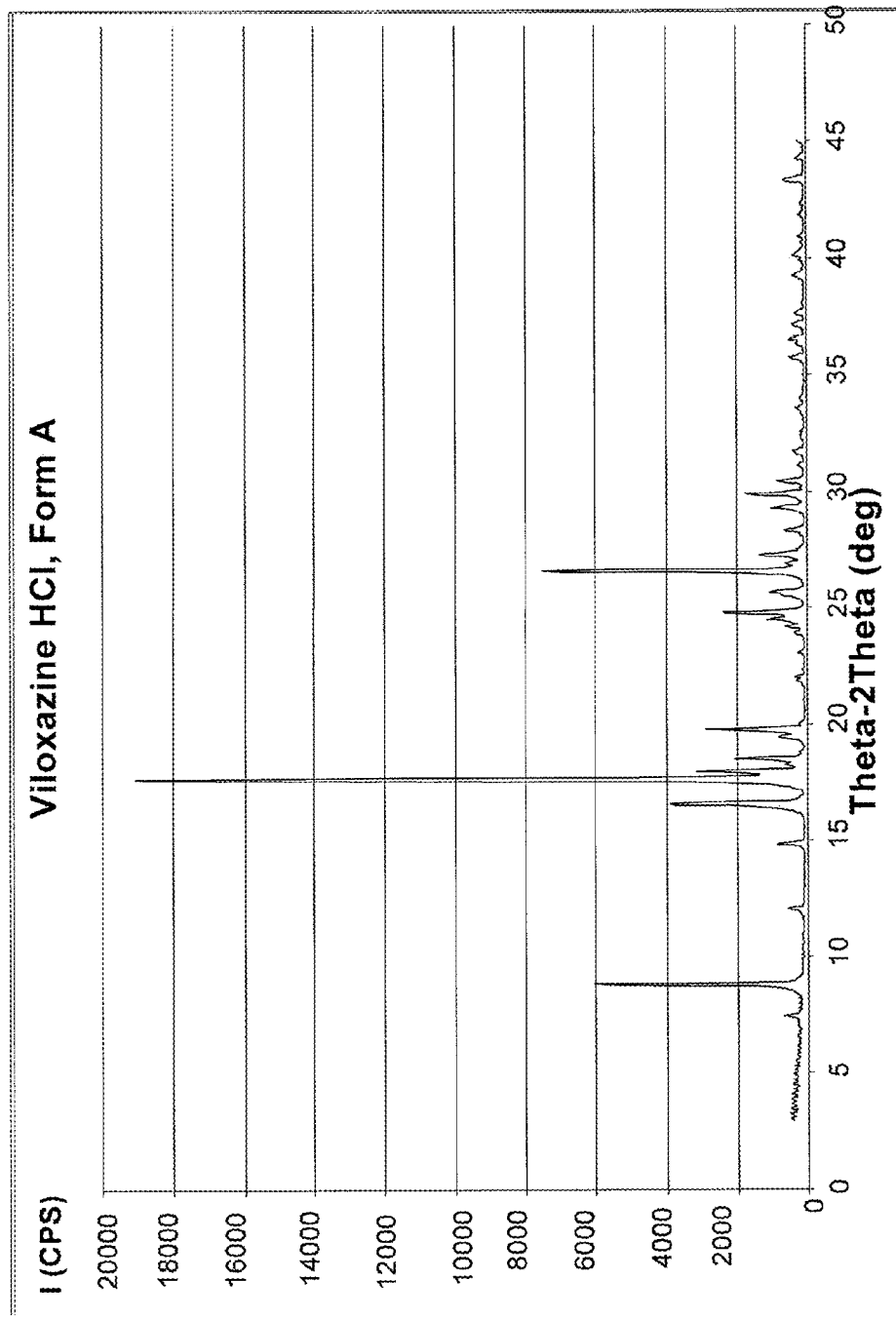
FIG. 6 shows an XRPD pattern of Viloxazine HCl, Form A.
Figure 7:
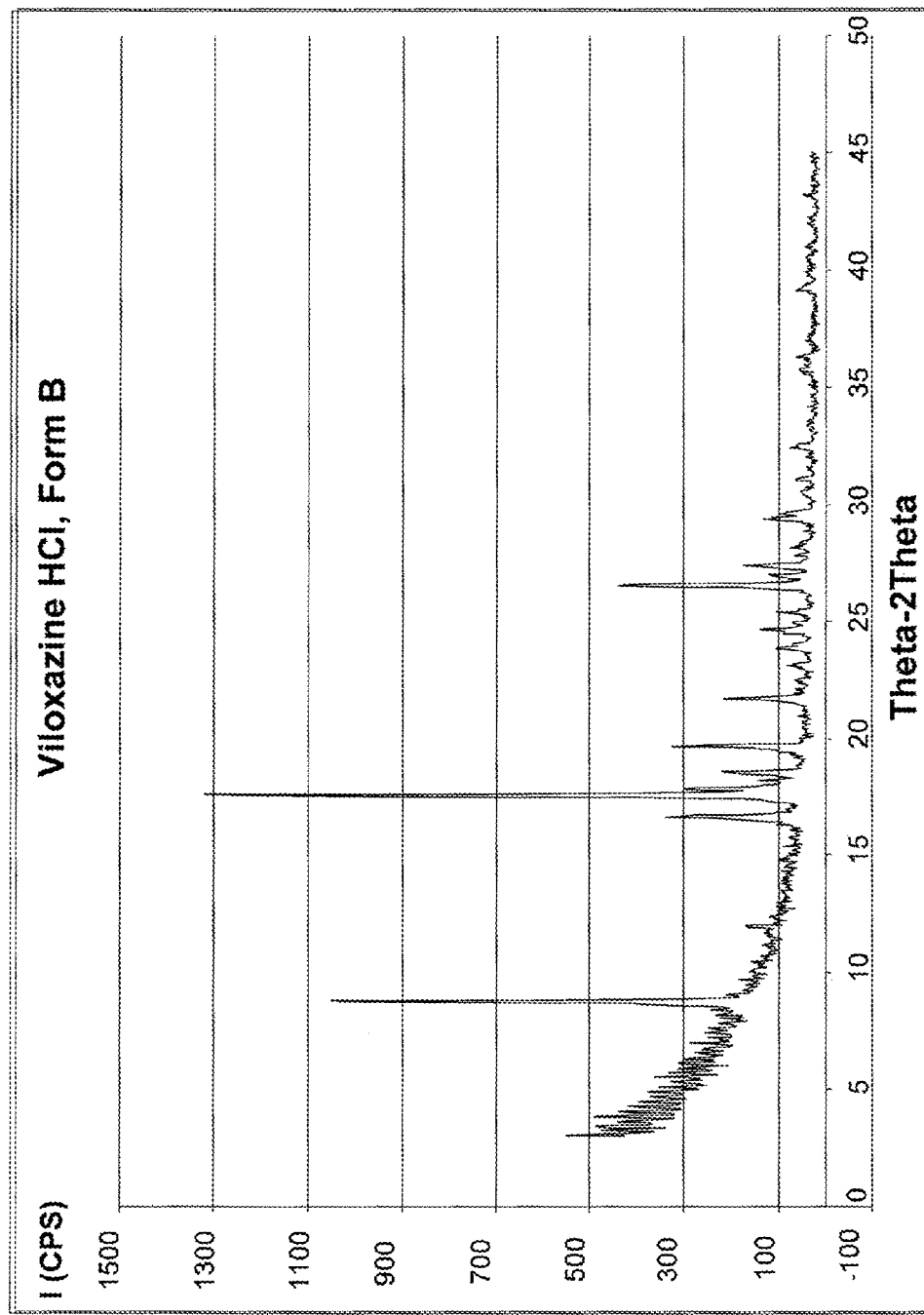
FIG. 7 shows an XRPD pattern of Viloxazine HCl, Form B.
Figure 9:
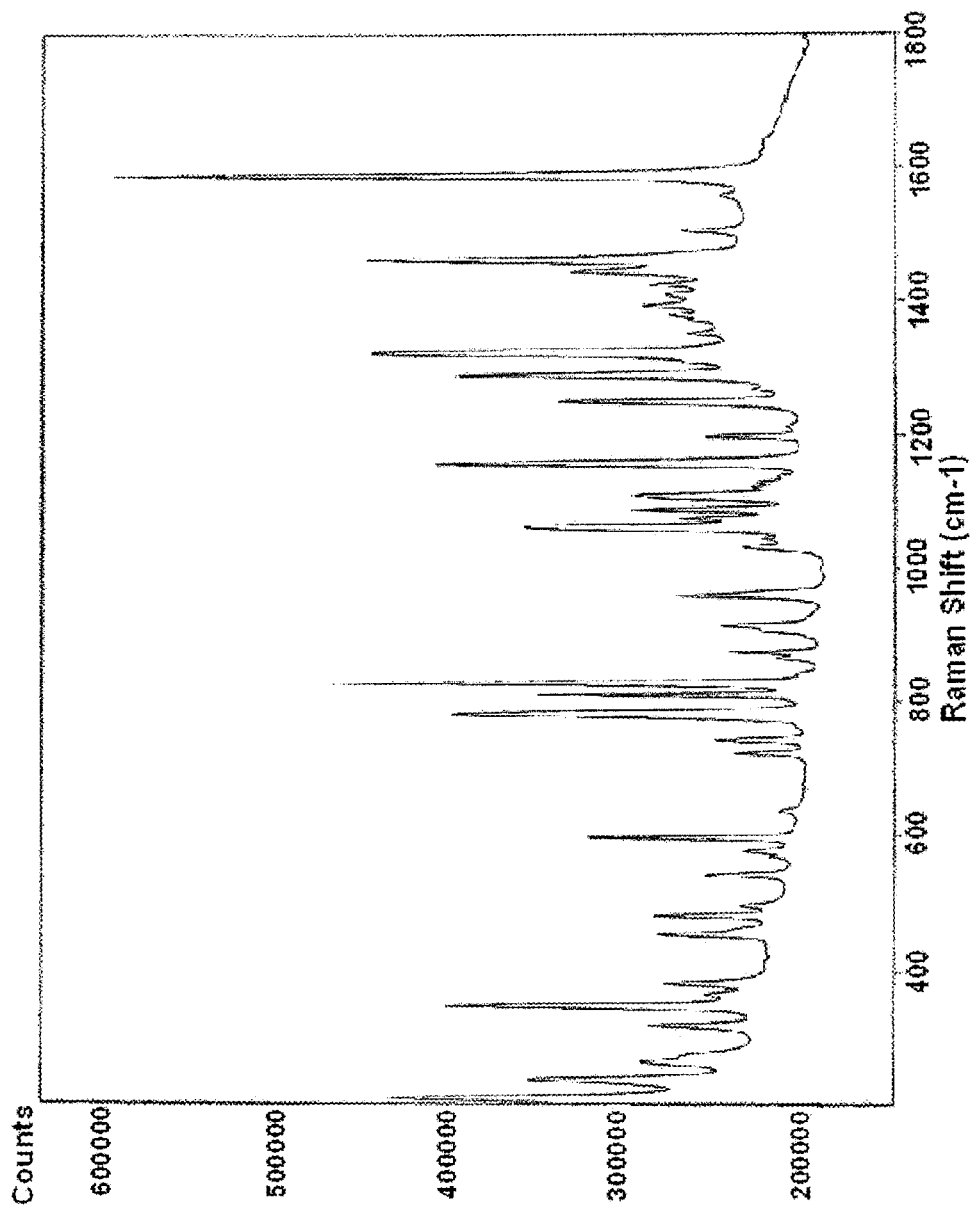
FIG. 9 shows a Raman spectrum of Viloxazine HCl, Form A.

In a further embodiment of the invention, unique crystalline forms of viloxazine were separated through binary-solvent crystallizations using a primary solvent selected from acetic acid, methanol (MeOH), ethanol (EtOH), dimethylformamide (DMF), and N-methylpyrrolidone (NMP) and an anti-solvent selected from acetonitrile, etyl acetate, acetone, methyl-t-butyl ether, tetrahydrofuran, toluene, dicloromethane (DCM) and heptan. Water may also be used as a primary solvent. In this case, the anti-solvent may be selected from methanol, ethanol, isopropyl alcohol (IPA), acetone, tetrahydrofuran (THF), dioxane, acetonitrile, dimethylformamide (DMF), and N-methylpyrrolidone (NMP). Two of these polymorphic forms of viloxazine HCl salt are designated here as anhydrous Form A and anhydrous Form B. Polymorph Form A is characterized by XRPD pattern and peaks and Raman spectrum and peaks as shown in FIG. 6 and FIG. 9; polymorph Form B is characterized by XRPD pattern and peaks and Raman spectrum and peaks as shown in FIG. 7 and FIG. 10. Physiochemical characterizations of the anhydrous Form A and anhydrous Form B of viloxazine HCl are shown in Example 45.

The inventors have also discovered that the polymorphic Forms A and B can be converted from one to another. Solvent composition can be a single solvent, a binary solvent system, a tertiary solvent system, a quaternary solvent system and so on. Different types of solvents, ratios of different solvents, ratio of solvents to viloxazine or viloxazine salt can be used to prepare or control or convert the forms. Various polymorphic forms of viloxazine salts including HCl salt having very low levels of impurities, especially toxic including genotoxic impurities, thus can be prepared, controlled or converted by the said polymorph forms preparation methods, or by combinations of the said synthetic methods, isolation and purification methods and the said polymorph forms preparation methods.

The non-excluding examples for the preparation of anhydrous Form A and anhydrous Form B of viloxazine HCl are given in Examples 20, 24, and 28 through 42. Stability of the said polymorphic forms is given in Examples 43-45.

In yet another aspect of the current invention, methods of synthesis of the main metabolites of viloxazine are provided. Compounds of Formula 6 and their salts thereof can be prepared through intermediates of Formula 7 (below).

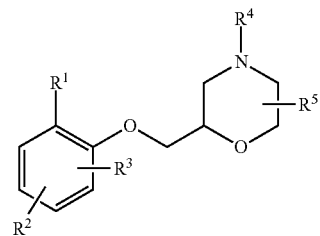

Formula 6 wherein, $R^1$, $R^2$, and $R^3$ are substituted or unsubstituted alkyl, alkenyl, alkynyl, aryl, arylalkyl, alkoxy, aryloxy, alkenoxy, alkynoxy, hydroxyl, halo, nitro, nitroso, carbonyl, carboxyl, amino, carboxamido, hydrogen, imino, cyanato, isocyanato, cyano, isocyano, pyridyl, pyrrolidyl, thio (thiol, substituted thio —S—R), disulfide (—S—S—H, —S—S—R), sulfonyl, sulfo, sulfinyl, thiocyanato groups; $R^4$ is substituted or unsubstituted alkyl, alkenyl, alkynyl, aryl, arylalkyl. carbonyl, hydrogen, pyridyl, pyrrolidyl groups; $R^5$ is a substituted or unsubstituted alkyl (e.g., benzyl herein is a substituted alkyl), alkenyl, alkynyl, aryl, alkoxy, aryloxy, alkenoxy, alkynoxy, hydroxyl, halo, nitro, nitroso, carbonyl, carboxyl, amino, carboxamido, hydrogen, imino, cyanato, isocyanato, cyano, isocyano, pyridyl, pyrrolidyl, thio (thiol, substituted thio —S—R), disulfide (—S—S—H, —S—S—R), sulfonyl, sulfo, sulfinyl, thiocyanato group, or =O. $R^1$, $R^2$, $R^3$, $R^4$ and $R^5$ used hereafter have the same meaning as described in Formula 6.

Precursors, pre-metabolites, and metabolites of viloxazine can be prepared by the methods disclosed herein. The precursors can be further converted to metabolites of viloxazine. For example, Compound E where Y=OH can be oxidized to form Compound D where Y=OH. Further, such compounds can be reacted or converted to produce other desirable derivatives (such as by glucuronidation on the OH groups of compounds disclosed herein). Exemplary embodiments of the current inventive methods and compounds are further illustrated in the non-limiting examples below. Some exemplary compounds A-E, illustrated below, in accordance with Formula 6 can thus be prepared:

Compound A

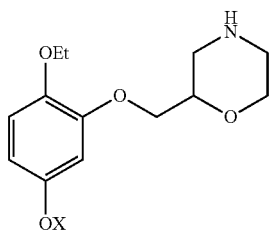

X = Bn, H

Compound B

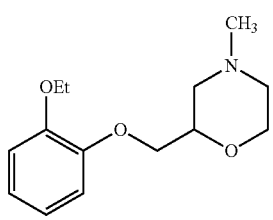

Compound C

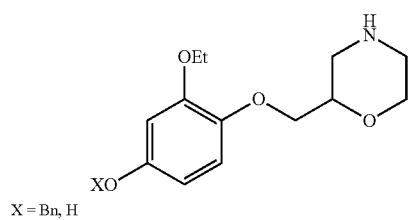

X = Bn, H

Compound D

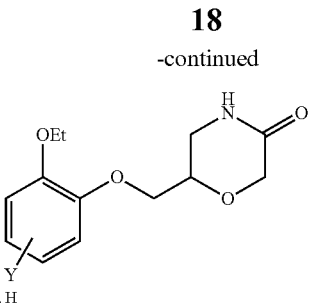

Y = Bn, OH, H

Compound E

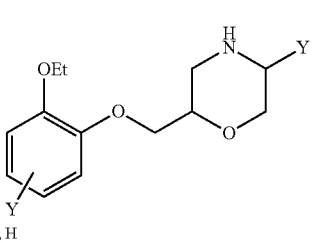

Y = Bn, OH, H

Formula 7

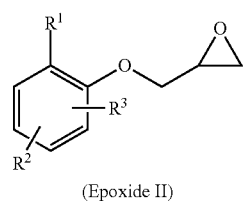

(Epoxide II)

Compounds of Formula 7 can be prepared from the corresponding compounds of Formula 8, which is illustrated below:

Formula 8

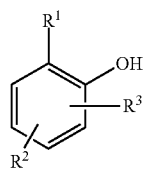

For example, Epoxide II (Formula 7) can be prepared by reacting compounds of Formula 8 with epichlorohydrin under conditions similar to those described for viloxazine preparation above. Optionally, Epoxide II may be reacted with a compound of Formula 9 or Formula 10 in the synthesis of the desired compound of Formula 6.

Formula 9

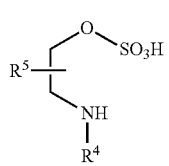

Formula 10

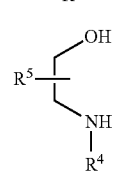

Further, the novel intermediate of Formula 11, illustrated below, can be prepared under the same conditions as those disclosed for the viloxazine synthesis.

Formula 11

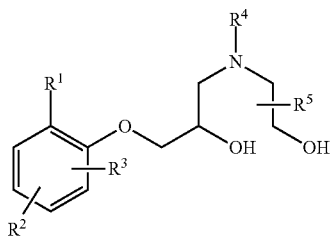

EXAMPLES

Example 1

Epoxide 1 Preparation in the Presence of a Solvent and a Phase-Transfer Catalyst Epichlorohydrin (4.0 eq.), potassium carbonate (powdered, 3.0 eq.), and tetrabutylammonium hydrogen sulfate (0.05 eq.) were charged to a clean reaction vessel and stirred to a uniform slurry. 2-Ethoxyphenol (1.0 eq.) dissolved in tert-butyl methyl ether (MTBE; 1.6 vol) was charged to the vessel. The reaction mixture was heated to 55° C., and stirred for a minimum of 16 hours (overnight). The reaction was then diluted with MTBE (6.25 vol) and quenched with water. The water layer was extracted three times using MTBE (2.1 vol), dried over sodium sulfate (1.0 wt/wt) and charcoal (0.05 wt/wt), filtered, and concentrated under reduced pressure to obtain an oil. The oil was co-evaporated with toluene multiple times to remove excess epichlorohydrin. This procedure resulted in crude yields of 98+%, and purity of 80-90% as determined by HPLC analysis.

Example 2

Epoxide 1 Preparation in the Presence of a Solvent and a Phase-Transfer Catalyst Near 100% yield and much greater purity of Epoxide 1 was achieved by limiting side reactions formed by the hydroxide ion by using a phase-transfer catalyst ("PTC"), a base, and a solvent. Further, the PTC reaction went to completion and proceeded to work-up much faster. This reaction utilized 2-ethoxyphenol (1 eq.), epichlorohydrin (4 eq.), and potassium carbonate powder (2 eq.), in MTBE (1 mL/g). The phase-transfer catalyst was tetrabutylammonium hydrogen sulfate (See Table 1 below).

TABLE 1

| Step 1 development - PTC results | | |
|---|---|---|
| Batch Size (2-Ethoxyphenol) | Amount of Final Product/Yield | Purity by HPLC |
| 1000 g | 1803 g/128.2% | 88.4% |
| 500 g | 698 g/99.3% | 88.1% |

The median yield for the PTC reactions was 99+%, with median purity by HPLC was measured at 88.2%. Excess epichlorohydrin was removed by co-evaporation with toluene. The reaction was stable in MTBE at room temperature or −20° C. over night. The crude material was stable at 53° C. during co-evaporation with toluene and stable at room temperature or −20° C. overnight.

Example 3

Epoxide 1 Preparation in the Presence of a Solvent and a Phase-Transfer Catalyst An appropriately sized three-neck round bottom flask was equipped with a mechanical stirrer, thermocouple with display, nitrogen inlet, condenser, and drying tube in a heating mantle. The following materials were charged into the flask: epichlorohydrin (1340 g, 14.48 mol, 1132 mL, 4.0 eq.), powdered potassium carbonate (1000 g, 7.24 mol, 2.0 eq.), and tetrabutylammonium hydrogen sulfate (61 g, 0.18 mol, 0.05 eq.). The mixture was stirred to an even slurry. Further, 2-ethoxyphenol (500 g, 3.92 mol, 459 mL, 1.0 eq.) in methyl tert-butyl ether (MTBE) (500 mL) were charged to the reaction mixture. The flask was heated to 45° C. for 48 hours with stirring. The reaction for checked completeness by HPLC. The starting material had Rt 8.875 minutes, product had Rt 10.025 minutes, intermediate had Rt 10.852 minutes, and an impurity had a Rt 13.975 minutes. The reaction was considered complete when a combined total of <5% of the starting material and intermediate were present in the reaction mixture. The contents were diluted with MTBE (1 L) and filtered the mixture through a glass fiber filter pad to remove insolubles. The organic mixture was washed with brine (3×800 mL) and the solution treated with charcoal and magnesium sulfate for 30 minutes. The solution and concentrate were filtered on a rotoevaporator at 35° C. The residue was co-evaporated with toluene (2×1 L). The product was an orange oil. 698 g, 99.3%, HPLC: 88.1%.

Example 4

Epoxide 1 Preparation in the Presence of a Solvent and a Phase-Transfer Catalyst and Conversion into Viloxazine Base A 6.1 kg batch of 2-ethoxyphenol was produced using 4.0 eq. of epichlorohydrin and 2.0 eq. of potassium carbonate at 45° C. provided a 60% conversion after 5 days. An additional 0.5 eq. of a phase-transfer catalyst (i.e. a benzyltriethylammonium salt) was added and the temperature was increased to 50° C. The following day, 82.5% conversion was obtained and the reaction was deemed complete. Assumed yield was 8.55 kg (100%), HPLC A %: 83.6% and G.C.: 62.4%. The intermediate was carried directly to the next step using 8.4 eq. of aminoethyl hydrogen sulfate and 30.0 eq. of potassium hydroxide (KOH). Adding the reaction mixture to the KOH solution resulted in 17% conversion and a recovery of 891 g of crude viloxazine after work up.

Example 5

Epoxide 1 Preparation in the Presence of a Solvent and a Phase-Transfer Catalyst and Conversion into Viloxazine Base A 6.1 kg batch of 2-ethoxyphenol was produced using 4.0 eq. of epichlorohydrin and 2.0 eq. of potassium carbonate at 50° C. provided a 63.7% conversion after two days. An additional 0.5 eq. of a phase transfer catalyst (i.e., a benzyltriethylammonium salt) was added and the following day 79.7% conversion was achieved and the temperature was increased to 55° C. The following day 80.2% conversion was obtained and the reaction was deemed complete. The crude oil was co-evaporated with toluene at 52° C. to remove excess epichlorohydrin. Yield was 7.2 kg, HPLC A %: 76.8%. The intermediate was carried directly to the next step using 8.4 eq. of aminoethyl hydrogen sulfate and 30.0 eq. of potassium hydroxide. Adding the intermediate mixture to 10.0 eq of KOH solution and stirring at 57° C. for 4 hours before adding the remaining 20.0 eq. of KOH solution resulted in 54.0% conversion the next day and a recovery of 4686 g of crude viloxazine after work up.

Example 6

Epoxide 1 Preparation in the Presence of a Solvent and a Phase-Transfer Catalyst and Conversion into Viloxazine Base A 9.6 kg batch of 2-ethoxyphenol was produced using 4.0 eq. of epichlorohydrin and 3.0 eq. of potassium carbonate at 55° C. provided 89.6% conversion after 24 hours. Assumed yield was 13.5 kg (100%), HPLC A %: 74.6%. The intermediate was carried directly to the next step using 8.4 eq. of aminoethyl hydrogen sulfate and 30.0 eq. of potassium hydroxide. Adding the intermediate mixture to 10.0 eq. of KOH solution and stirring at 57° C. for 4 hours before adding the remaining 20.0 eq. of KOH solution resulted in 52.3% conversion the next day and a recovery of 4.7 kg of crude viloxazine after work up.

Example 7

Epoxide 1 Preparation in the Presence of a Solvent and a Phase-Transfer Catalyst and Conversion into Viloxazine Base A 12 kg batch of 2-ethoxyphenol was produced using 4.0 eq. of epichlorohydrin and 3.0 eq. of potassium carbonate at 55° C. provided 77.6% conversion after 24 hours. Assumed yield was 16.8 kg (100%), HPLC A %: 79.7%. 9.7 kg of the intermediate was carried directly to the next step using 8.4 eq. of aminoethyl hydrogen sulfate and 30.0 eq. of potassium hydroxide. Adding the intermediate mixture to 10.0 eq. of KOH solution and stirring at 57° C. for four hours before adding the remaining 20.0 eq. of KOH solution resulted in 52.3% conversion the next day and a recovery of 2.6 kg of crude viloxazine after work up.

Example 8

Epoxide 1 Preparation in the Presence of a Solvent and a Phase-Transfer Catalyst The 2-ethoxyphenol may require melting prior to use. The following procedure was performed: into a clean dry 50 gallon glass lined reactor epichlorohydrin (25.7 kg), potassium carbonate (28.8 kg) and tetrabutylammonium sulfate (1.18 kg) were charged under nitrogen with stirring. This mixture was stirred to an even slurry. 2-ethoxyphenol (9.6 kg) dispersed in MTBE (15 L) was added to the slurry. The resulting slurry to was heated 55° C. and held at this temperature for a minimum of 16 hours. The reaction mixture may be monitored by HPLC if desired, but based on historical data, after a minimum of 16 hours the reaction is complete. The reaction mixture was checked for reaction completion by HPLC. The sample was worked-up by adding water (2.0 vol.) and MTBE (2.0 vol.), mixing well, and separating organic layer for HPLC (PRLC6-230 nm). Starting material Rt 8.875 minutes, product Rt10.025 minutes, intermediate Rt 10.025 minutes, and an impurity Rt 13.975 minutes. The reaction was deemed complete when a combined total of <5% of starting material and intermediate were present in the reaction mixture. MTBE (60 L) was added and stirred 15 minutes. Water (30 L) was added and stirred for a minimum of 30 minutes. Stirrer stopped and layers allowed to separate for a minimum of 15 minutes. Bottom aqueous phase removed (held for back extraction This step was repeated three times. The aqueous phase was back extracted with MTBE (20 L) and stirred for a minimum of 30 minutes; layers allowed to separate for a minimum of 15 minutes. Bottom aqueous phase removed (this may be disposed of properly). 25% aqueous sodium chloride (30 L) was added to the combined organics and stirred for a minimum of 30 minutes; layers allowed to separate for a minimum of 15 minutes. Bottom aqueous sodium chloride phase removed (this may be disposed of properly). Sodium sulfate (4.0 kg) was added and stirred a minimum of one hour. Activated carbon (0.5 kg) was added and stirred a minimum of one hour. Filtered off the sodium sulfate and carbon and washed with MTBE (10 L). The resulting filtrate was stripped to a thick oil under vacuum at 35° C. and co-evaporated with toluene (3×4 L) under vacuum to a pot temperature of 52° C. yield/13.6 kg (100%) HPLC Area %: 74.6% G.C.: 51.5%. Material may be carried directly to the next step.

Example 9

Epoxide 1 Preparation in the Presence of a Solvent, a Phase-Transfer Catalyst and an Additional Catalyst Provide 1 eq. of 2-ethoxyphenol, 1.0-2.0 eq. of epichlorohydrin, 2 eq. of powdered potassium carbonate powder (325 mesh), 0.001-0.05 eq. of tetrabutylammonium salt $Q^+X^-$ ($X=HSO_4$ or Cl), 0.0005-0.025 eq. of potassium iodide (catalyzes the process via the Finkelstein reaction when used in the amount that doesn't exceed the amount of $Q^+X^-$; use ~50% in regards to $Q^+$). If amount of $I^-$ is equal or greater to the amount of $Q^+X^-$, a strong inhibition of the reaction is observed; 1-10 vol. of acetonitrile (solvent to dissolve the tetraalkylammonium salt of the substrate). It is recommended to use a minimal volume of solvent to make the reaction mixture stirrable to ensure the highest reaction rate (DCM is not recommended as the solvent because it reacts with phenolates); 20-50° C., 12-48 hrs. Use the lowest temperature possible to ensure reasonable reaction rate and minimize unwanted side reactions. Typical work-up conditions are similar to the described above.

Example 10

Epoxide 1 Preparation at Low Temperature

The reaction of 2-ethoxyphenol and epichlorohydrin at room temperature in presence of sodium hydroxide solution was improved. In one instance, the reaction of 2-ethoxyphenol (1 eq.) and epichlorohydrin (1.5 eq.) in water and 50% NaOH solution (1.2 eq.) was stirred at room temperature over night. The second step took the intermediate from the first step and coupled it with 2-aminoethyl hydrogen sulfate (2.12 eq.) in 50% NaOH (4.24 eq.), water, and ethanol. The overall yield using this route was a median of 19.2% after re-crystallization to achieve the desired purity. Experiments were conducted to maintain the reaction mixture at <10° C. during the overnight stir period (See Table 3, below).

TABLE 2

Step I Experimental Conditions at Ambient Temperature Overnight

| Batch Size (2-Ethoxyphenol) | Amount of Intermediate/Yield | Purity by HPLC |
|---|---|---|
| 200 g | 257 g/84.8% | 57.3% |

TABLE 3

Step I Experimental Conditions at 5-8° C.

| Batch Size (2-Ethoxyphenol) | Amount of Intermediate/Yield | Purity by HPLC |
|---|---|---|
| 1000 g | 1499 g/107% | 66.2% |
| 200 g | 277 g/91.4% | 48.5% |
| 200 g | 275 g/90.7% | 55.8% |

This resulted in an increase in Step I yield. However, the best initial purity results remained at only 48.5% to 66.2% with multiple side products forming.

Example 11

Epoxide 1 Preparation Through the Finkelstein Reaction

Alternatively, Epoxide 1 can be prepared by using a Finkelstein reaction catalyst, such as KI. The base can be used as a solid. An aprotic solvent can be used. 1 eq. of 2-ethoxyphenol, 1.0-2.0 eq. of epichlorohydrin, 2 eq. of potassium carbonate powder (~325 mesh), 0.2 eq. of potassium iodide (which catalyzes the process via the Finkelstein reaction), 5 vol. of DMF (polar aprotic solvent to dissolve the potassium salt of the substrate and make it reactive), 20-30° C., 12-48 hrs. Typical work-up conditions include the following steps: (1) Pour the reaction mixture onto a stirred mixture of heptane (8 vol.), EtOAc (2 vol.) and water (15 vol.); (2) stir the mixture over 5-10 minutes, allow the layers to separate, and collect the organic layer; (3) extract the aqueous layer with a mixture of heptane (4 vol.) and EtOAc (1 vol.); (4) combine all organic layers and wash with water (3×3 vol.) to remove any residual DMF; (5) dry the organic solution with $MgSO_4$ (0.2 vol) over 10-15 minutes with stirring; (6) filter off $MgSO_4$ and rinse the filter cake with a mixture of heptane (0.8 vol.) and EtOAc (0.2 vol.); (7) concentrate the filtrate under reduced pressure at 35-45° C. to a minimal stirring volume; (8) co-evaporate the residue with heptane (2×2 vol.) under reduced pressure at 40-45° C. to remove residual EtOAc (if needed); and (9) recrystallize the residue from a suitable solvent (if applicable) or use directly in the next step as is.

Example 12

Epoxide 1 Preparation in a 2-Stage PTC Process

The following steps were performed: equipping a 1 L three-neck glass-reactor with a mechanical stirrer, thermocouple with display, nitrogen inlet, condenser, and under vacuum distillation system and then performing the following: Under stirring, charging to the flask epichlorohydrin (313.44 g, 3.3878 mol, 265.36 mL, 8.05 eq.) and 2-ethoxyphenol (58.17 g, 0.4210 mol, 53.37 mL, 1.0 eq.). Heating the flask to 60° C. Adding solid benzyl triethylammonium chloride (9.65 g, 0.0424 mol, 0.1 eq.) and heating the flask to 70° C. for 6 h. Checking the reaction for completeness by TLC. Preparing the sample by taking a 1 mL aliquot of the reaction mixture and diluting to a clear solution with acetone to obtain a 5% solution. Using 7:3 heptane/ethyl acetate or the eluent. The starting material was Rf 0.77 and the intermediate was Rf 0.58. The reaction was deemed complete when there was no starting material in the reaction mixture. Concentrating the reaction mixture at 70° C. under vacuum. Cooling down to 45° C. Diluting the residue with toluene (145.46 g). Adding dropwise in 20 min NaOH aq. 30% (73.27 g, 0.5495 mol, 1.305 eq.) and stirring at 45° C. for 1 h after addition. Washing the organic mixture with water (3×75.6 g) and concentrating under vacuum at 70° C. The product was a pale yellow oil which was used without any further purification in the next step. 84.63 g, 103.5%, GC: 97.3% area.

Example 13

Conversion of Epoxide 1 into Viloxazine Base

2-Aminoethyl hydrogen sulfate (8.4 eq.) was dissolved in 60% aq. potassium hydroxide solution (10.0 eq.). After a uniform solution was achieved, the Step I intermediate (Epoxide 1, 1 eq.) diluted in methanol (9.8 vol) was added. The reaction mixture was stirred at 55° C. for 4 hours, 60% aq. potassium hydroxide solution (20.0 eq.) was added and then stirred at 55° C. for a minimum of 16 hours (overnight). The reaction was deemed complete by HPLC when the reaction progress showed 50-55% of desired product. The reaction was then worked up as described in Step IIa below. This exemplary procedure produces averaged yields of 30-40% with purity of crude product >80% by HPLC.

Exemplary work-up steps of this method were as follows: Stripped the methanol to a pot temperature of 50° C. under vacuum. Added water (20.8 vol) to the thick slurry. Transferred the slurry to water (72.9 vol.). Added MTBE (9.4 vol) and stir 15 minutes. Stopped stirrer and allowed layers to separate for a minimum of 15 minutes. Separated phases (hold organic phase). If un-dissolved salt remains, added recorded amount of water to help dissolve the salt. If resultant solution was hazy, filtered the resultant solution through a filter funnel or centrifuge to allow for better separation. Extracted aqueous phase with MTBE (9.4 vol) and stirred 15 minutes. Stopped stirrer and allowed layers to separate for a minimum of 15 minutes. Separated phases (held organic phase). Extracted aqueous phase with MTBE (9.4 vol) and stirred 15 minutes. Stopped stirrer and allowed layers to separate for a minimum of 15 minutes. Separated phases (held organic phase). Extracted aqueous phase with MTBE (9.4 vol) and stirred 15 minutes. Separated phases. Checked aqueous phase for the presence of product. Further extractions may have been required. Combined the organics and washed with 20% brine solution. Separated layers. Cooled the organics to 5-10° C. Extracted the combined organics with 6 M HCl (40 L). Stirred for 15 minutes. Stopped stirrer and allowed layers to separate for a minimum of 15 minutes. Separated phases (held aqueous phase). Extracted the combined organics with 6 M HCl (20 L). Stirred for 15 minutes. Stopped stirrer and allowed layers to separate for a minimum of 15 minutes. Separated phases (held aqueous phase). Extracted the combined organics with 6 M HCl (20 L). Stirred for 15 minutes. Stopped stirrer and allowed layers to separate for a minimum of 15 minutes.

Separated phases. Checked organic phase for the presence of product. Further extractions may have been required.

Slowly added 50% sodium hydroxide to the combined aqueous phase at <25° C. to a pH >12. Extracted aqueous phase with MTBE (30 L) and stirred 15 minutes. Stopped stirrer and allowed layers to separate for a minimum of 15 minutes. Separated phases (held organic phase). Extracted aqueous phase with MTBE (30 L) and stirred 15 minutes. Stopped stirrer and allowed layers to separate for a minimum of 15 minutes. Separated phases (held organic phase). Extracted aqueous phase with MTBE (30 L) and stirred 15 minutes. Stopped stirrer and allowed layers to separate for a minimum of 15 minutes. Separated phases (held organic phase). Extracted aqueous phase with MTBE (30 L) and stirred 15 minutes. Stopped stirrer and allowed layers to separate for a minimum of 15 minutes. Separated phases (held organic phase). Combined the organics and washed with 20% brine solution. Added sodium sulfate to the combined organics and stirred a minimum of one hour. Added activated carbon (0.05 eq.) and stirred a minimum of one hour. Filtered off the sodium sulfate and carbon and washed with MTBE (1.0 vol.). Stripped the resulting filtrate to a thick oil under vacuum at 35° C. Added isopropanol (1.45 vol.) to the oil. Added conc. HCl at a pot temperature <25° to a pH 1. Added ethyl acetate (5.6 vol.) to the mixture. Cooled to −5° C. and stirred for a minimum of 12 hours. Filtered the solid product. Washed the resulting solids with 0° C. isopropanol (2×0.78 vol.). Further washed the solids with ethyl acetate (2×1.05 vol.). Oven dried the solids to a constant weight at 35° C. under vacuum.

Example 14

Conversion of Epoxide 1 into Viloxazine Base

Step II a reaction was improved by reacting of 1 eq. of Epoxide 1 with 2-aminoethyl hydrogen sulfate (8.4 eq.) in a large molar excess of potassium hydroxide solution (30 eq.). See Table 4 below.

TABLE 4

| Step IIa - Experimental Results | | |
|---|---|---|
| Batch Size (Step 1 int.) | Amount of Final Product/Yield | Purity by HPLC |
| 260 g | 114 g/31.1% | 99.2% |
| 1406 g | 788 g/39.8% | 99.1% |
| 277 g | 127 g/32.4% | 99.1% |

Example 15

Conversion of Epoxide 1 into Viloxazine Base

An appropriately sized three-neck round bottom flask was equipped with a mechanical stirrer, thermocouple with display, and a nitrogen inlet and placed initially in a cooling tub. Potassium hydroxide (802 g, 14.30 mol, 10 eq.), water (500 mL) and 2-aminoethyl hydrogen sulfate (1695 g, 12.01 mol, 8.3 eq.) were charged in and stirred to an even solution under a nitrogen atmosphere, maintain the temperature under 55° C. 1-(Ethoxyphenoxy)-2,3-epoxypropane (starting intermediate) (277 g, 1.43 mol, 1.0 eq.), and methanol (2.2 L) were charged to the flask and heated to 55° C. for 4 hours. Potassium hydroxide (1604 g, 28.60 mol, 20 eq.) in water (1.1 L) was charged to the flask and stirred at 55° C. for 16 hours. The reaction was checked for completeness by TLC. The sample was prepared by taking a 0.5 mL aliquot of the reaction mixture and diluting to a clear solution with water, then extracting with ethyl acetate. The organic layer was compared to the starting intermediate from Step I using 1:1 heptane/ethyl acetate as an eluent. The starting material was $R_f$ 0.7 and the product was $R_f$ 0.0. The reaction was deemed complete when there is no starting material in the reaction mixture. The reaction mixture was concentrated to remove methanol.

Example 16

Preparation of
2-[(2-ethoxyphenoxy)methyl]morpholine
hydrochloride (viloxazine HCl)

Exemplary Procedure included the following: (1) Charging to a clean 100 gallon stainless steel reactor water (57.9 L) with stirring under nitrogen. (2) Adding potassium hydroxide pellets (78.0 kg) at <50° C. (3) Cooling solution to 20-25° C., dropped out of reactor and held for step 10; labeling accordingly. (4) Charging the stainless steel reactor with water (26.2 L). (5) Adding potassium hydroxide pellets (38.9 kg) at <50° C. (6) Adding 2-aminoethyl hydrogen sulfate (82.4 kg). (7) Heating the resulting mixture to 55° C. (8) Adding to the oil from previous step, 1-(ethoxyphenoxy)-2,3-epoxypropane, methanol, (94.5 L) and transferring to the mixture, step 7 (below), in the stainless steel reactor at 55° C. (9) Stirring at 55° C. for 4 hours. (10) Adding the prepared potassium hydroxide solution from step 3 (above) to the reaction mixture at less than 60° C. (11) Stirring the mixture at 57° C. for a minimum of 12 hours. (12) Sampling the reaction mixture for reaction completion check by HPLC. Working-up sample by adding water (8.0 vol.) and MTBE (2.0 vol.), mixing well and separating organic layer for HPLC (PRLC 6-230 nm). Starting material Rt 10.0 minutes, product Rt 7.0 minutes, intermediate Rt 10.025 minutes, and impurities at Rt 13.975 minutes and Rt 6.4 minutes. (13) Typically 45-55% product was present. Stirring longer has not improved the conversion percentage. The HPLC monitoring is recommended for informational purposes only, as the reaction has proven to proceed to a point of completion after 12-16 hours of heating and will not progress further even with additional reagents, base, or time. (14) Stripping off the MeOH to a pot temperature of 50° C. under vacuum. (15) Adding water (200 L) to the thick slurry. (16) Transferring the slurry to water (700 L). Solution will occur. (17) Adding MTBE (90 L) and stirring 15 minutes. (18) Stopping stirrer and allowing layers to separate for a minimum of 15 minutes. (19) Separating phases (held organic phase). (20) Extracting aqueous phase with MTBE (90 L) and stirring 15 minutes. (21) Stopping stirrer and allowing layers to separate for a minimum of 15 minutes. (22) Separating phases (held organic phase). (23) Extracting aqueous phase with MTBE (90 L) and stirring 15 minutes. (24) Stopping stirrer and allowing layers to separate for a minimum of 15 minutes. (25) Separating phases (held organic phase). (26) Extracting aqueous phase with MTBE (90 L) and stirring 15 minutes. (27) Separating phases. Checking aqueous phase for the presence of product. Further extractions may have been requiring. (28) Extracting the combined organics with 6 M HCl (30 L). (29) Stirring for 15 minutes. (30) Stopping stirrer and allowing layers to separate for a minimum of 15 minutes. (31) Separating phases (held aqueous phase). (32) Extracting the combined organics with 6 M HCl (15 L). (33) Stirring for 15 minutes. (34) Stopping stirrer and allowing layers to separate for a minimum of 15 minutes. (35) Separating phases (held aqueous phase). (36) Extracting the combined organics with 6 M HCl (15 L). (37) Stirring for 15 minutes. (38) Stopping stirrer and allowing layers to separate for a minimum of 15 minutes. (39) Separating phases. Checking organic phase for the presence of product. Further extractions may have been required. (40) Adding 50% sodium hydroxide (20 L) to the combined aqueous phase at <25° C. to a pH >12. (41) Extracting aqueous phase with MTBE (30 L) and stirring 15 minutes. (42) Stopping stirrer and allowing layers to separate for a minimum of 15 minutes. (43) Separating phases (held organic phase). (44) Extracting aqueous phase with MTBE (30 L) and stirring 15 minutes. (45) Stopping stirrer and allowing layers to separate for a minimum of 15 minutes. (46) Separating phases (held organic phase). (47) Extracting aqueous phase with MTBE (30 L) and stirring 15 minutes. (48) Stopping stirrer and allowing layers to separate for a minimum of 15 minutes. (49) Separating phases (held organic phase). (50) Extracting aqueous phase with MTBE (30 L) and stirring 15 minutes. (51) Stopping stirrer and allowing layers to separate for a minimum of 15 minutes. (52) Separating phases (held organic phase). (53) Adding sodium sulfate (8.0 kg) to the combining organics and stirring a minimum of 1 hour. (54) Adding activated carbon (0.5 kg) and stirring a minimum of 1 hour. (55) Filtering off the sodium sulfate and carbon and washing with MTBE (10 L). (56) Stripping the resulting filtrate to a thick oil under vacuum at 35° C. (57) Adding isopropanol (14 L) to the oil. (58) Adding conc. HCl (3.1 L) at a pot temperature <25° to a pH 1. (59) Adding ethyl acetate to the mixture. (60) Cooling to −5° C. and stirring for a minimum of 12 hours. (61) Filtering the solid product. (62) Washing the resulting solids with 0° C. isopropanol (2×7.5 L). (63) Further washing the solids with ethyl acetate (2×10 L). (64) Oven drying the solids to a constant weight at 35° C. under vacuum. Crude yield: 5.6 kg; HPLC: 72.7%.

Example 17

Formation and Cyclization of Diol 1

The following was performed in a 1 liter three-neck glass-reactor equipped with a mechanical stirrer, thermocouple with display, nitrogen inlet, condenser, and under vacuum distillation system: Under stirring, charging to the flask crude 1-(ethoxyphenoxy)-2,3-epoxypropane (intermediate) (84.63 g.) and toluene (245 mL) to the flask and heating to 100° C. Adding dropwise 2-benzylaminoethanol (66.01 g, 0.4365 mol, 1.037 eq.) to the flask and heating at reflux for 6 hours. Checking the reaction for completeness by HPLC. The reaction was deemed complete when there was less than 2% starting material in the reaction mixture. Cooling down the reaction mixture to room temperature. Adding toluene (130 mL) and solid benzyltriethylammonium chloride (4.99 g, 0.0219 mol, 0.052 eq.). Adding NaOH micro-pellets (104.62 g, 2.6155 mol, 6.213 eq.). The reaction mixture became very thick. After stirring 10 min at room temperature, slowly adding solid para-toluenesulfonyl chloride (84.71 g, 0.4443 mol, 1.055 eq.) by keeping the temperature below 40° C. Stirring for 2 h at room temperature. Checking the reaction for completeness by HPLC (Rt 8340 DI=15.9', Rt 8340Bn=17.3'). Washing the organic mixture with water (1×507.06 g+2×130.98 g) and concentrating under vacuum at 45° C. The product was a pale yellow oil which may be used without any further purification in the next step. 137.85 g, 113.5%, HPLC: 67.8% area.

Example 18

Deprotection and Crystallization of Viloxazine

The following was performed in a 1 liter three-neck glass-reactor equipped with a mechanical stirrer, thermocouple with display, nitrogen inlet, condenser, and under vacuum distillation system: Under stirring, charging to the flask crude N-benzylviloxazine (intermediate) (137.85 g.), ethanol (295 mL), HCl aq. 32% (135.6 mL), $H_2O$ (135.6 mL) and Pd/C 3% (75.84 g.). Heating the flask to 60° C. Bubbling $H_2$ in the reaction mixture (time of the bubbling depends on the size of the $H_2$ bubbles: with very small bubbles, reaction is finished after 2 h). Checking the reaction for completeness by HPLC (Rt viloxazine=11.7'). Concentrating the reaction mixture under vacuum to dryness. Adding to the residue isopropanol (290 mL) and water (60 mL). Heating the mixture to 80° C. until solution occurs. Slowly cooling the solution to 50° C. and slowly adding ethyl acetate (480 mL). Cooling the mixture to 0-5° C. for at least 3 h. Filtering the product and washing with ethyl acetate (2×50 mL). Vacuum oven driing the solids at 80° C. to constant weight. 52.24 g, 57.0%, HPLC: 99% assay.

Example 19

Viloxazine HCl (6089 g) was dissolved in water (10 vol.). Free-basing of the salt was performed by slow addition of 50% NaOH (temp. <25° C.) to the solution until pH 11 is reached. Once the free base was formed, it was extracted three times with methyl tert-butyl ether (MTBE, 5 vol. per extraction). The combined MTBE extracts were then washed with water (1.5 vol.). The resultant organics were then dried over sodium sulfate (1.0 eq.), filtered through an in-line cartridge, and the sodium sulfate washed with MTBE (1.0 vol). The organics were then concentrated down to a thick oil.

Example 20

Conversion Between Viloxazine Base and Viloxazine Salt; Formation of Polymorph Form B The residue from Example 15 was diluted with water (30 L) and extracted with ethyl acetate (6×2 L). All organic extracts were combined and further extracted with 6 M HCl (3×2 L). The organic layer was checked for product by TLC and then discarded. The aqueous solution was adjusted to pH 12 with 50% NaOH. The basic solution was extracted with MTBE (3×3 L). All organic extracts were combined and washed with brine (1 L), and then treated with charcoal and magnesium sulfate for 30 minutes. The mixture was filtered through a glass fiber filter pad and concentrated on a roto-evaporator at 45° C. to give a light-colored oil. The residue was diluted with ethyl acetate (1 L) and 12 M HCl (80 mL) in isopropanol (160 mL), and stirred for 30 minutes at 0-5° C. The product was filtered and washed with ethyl acetate (2×400 mL) and heptane (3×500 mL). The solids were dried in a vacuum oven at 40° C. to constant weight. 127 g, 32.4%, HPLC: 94.6%.

Example 21

Recrystallization; Formation of Polymorph Form A

Example 21 A

The following method was performed as needed; typically twice: Charged isopropanol (1.5 vol.), water (0.75 vol.), and crude viloxazine HCl (1.0 eq.) to a clean dry reactor with stirring under nitrogen. Heated the mixture to 80° C. Solution occurred. Hot filtered the resultant solution. Cooled the solution to 45-50° C., solids began to precipitate. Slowly added ethyl acetate (4.0 vol.). Cooled the mixture to −5°-0° C. and stirred for a minimum of 12 hours. Filtered the resulting solids. Washed the solids with 0° C. Isopropanol (2×1 vol). Washed the solids with 0° C. ethyl acetate (2×1 vol.). Oven dried the solids to a constant weight at 35° C. under vacuum.

Example 21 B

The following method was performed as needed; typically twice: Charged isopropanol (4.5 vol.) at 80° C. to a clean dry reactor with stirring under nitrogen. Add water (1 vol); bring the temperature to 45-50° C. Add viloxazine. Slowly added ethyl acetate (7.0 vol.). Cooled the mixture to 0-5° and stirred for a minimum of 2.5 hours. Filtered the resulting solids. Washed the solids with ethyl acetate (2×1 vol.). Oven dried the solids to a constant weight at 35° C. under vacuum.

Figure 8:
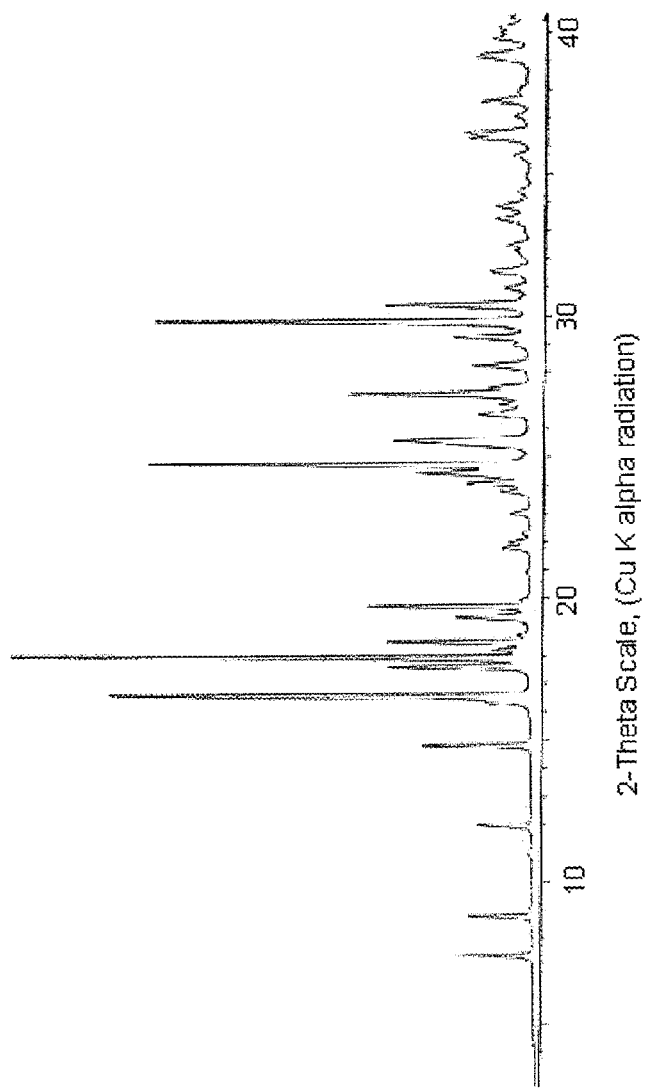
FIG. 8 shows an XRPD pattern of recrystallized Viloxazine HCl, Form A.

The resultant product was white to off-white powder comprising not more than 2.1 ppm of 1-(ethoxyphenoxy)-2,3-epoxypropane and not more than 2.1 ppm of epiclorhydrine. The product was identified through IR spectrum, HPLC and XRPD (FIG. 8).

Example 22

Conversion Between Viloxazine Base and Viloxazine Salt, and Recrystallization

Purification according to methods described in Examples 19 and 21 afforded substantially pure viloxazine HCl with extremely low levels of epichlorohydrin, 1-(ethoxyphenoxy)-2,3-epoxypropane and 2-aminoethyl hydrogen sulfate. No trace of aminoethyl hydrogen sulfate ester of an alcohol was observed. Typical analytical results for exemplary batches provided by the methods of this Example are provided in Table 5, below.

TABLE 5

| Batch Analysis Summary | | | |
|---|---|---|---|
| | Epichlorohydrin | 1-(ethoxyphenoxy)-2,3-epoxypropane | 2-aminoethyl hydrogen sulfate |
| Sample 1 of GMP lot used for clinical trial material manufacturing | 0.6 ppm | None Detected | None Detected |

Example 23

Formation of Polymorph B

The oil from Example 19 was dissolved in isopropanol (IPA, 1.0 vol), adjusted to pH=1 with conc. HCl (2 vol), and ethyl acetate added (EtOAc, 3.7 vol). The resultant slurry was then cooled to −5 to 0° C., and stirred for a minimum of 12 hours. The slurry was then filtered, washed with cold IPA (2×0.5 vol), and then cold EtOAc (2×1.5 vol). The isolated solid was then dried under vacuum at 35-40° C.

Example 24

Formation of Polymorph A; Conversion from B to A

Viloxazine HCl (crude, or in Form B) was re-dissolved in IPA (1.5 vol.) and water (0.75 vol.) at −80° C., cooled to 45-55° C., and EtOAc (4.0 vol) was added. The solution was cooled to cool to −5 to 0° C., and stirred for a minimum of 12 hours. The slurry was then filtered, washed with cold IPA (2×0.5 vol.), and then cold EtOAc (2×1.5 vol.). The isolated solid was then dried under vacuum at 35-40° C.

Example 25

Purification steps included the following: (1) Charged isopropanol (8.3 L/1.5 vol.), water (4.1 L/0.75 vol.), and crude viloxazine HCl (5.5 kg) to a clean dry 50 gallon reactor with stirring under nitrogen. (2) Heated the mixture to 80° C. Solution occurred. (3) Cooled the solution to 50° C., solids began to precipitate. (4) Slowly added ethyl acetate (22.0 L/4 vol.). (5) Cooled the mixture to −5°-0° C. and stir for a minimum of 12 hours. (6) Filtered the resulting solids. (7) Washed the solids with 0° C. isopropanol (5.5 L/1 vol). (8) Washed the solids with ethyl acetate (2×5.5 L/2 vol.). (9) Oven dried the solids to a constant weight at 35° C. under vacuum. Yield/4.7 kg-HPLC/98.8%.

TABLE 6

| Crude (g) | Yield (g) | HPLC |
|---|---|---|
| 11,187 g | 9088 g/81.2% | 98.2% |
| 5600 g | 4619 g/82.5% | 98.8% |
| 2601 g | 2176 g/83.6% | 98.4% |

Example 26

High purity purification steps included the following: (1) Charging isopropanol (10.2 L/1.5 vol.), water (5.1 L/0.75 vol.), and >98.0% viloxazine HCl (6.816 kg) to a clean dry 50 gallon reactor with stirring under nitrogen. (2) Heating the mixture to 80° C. Solution occurred. (3) Cooling the solution to 50° C., solids began to precipitate. (4) Slowly adding ethyl acetate (27.3 L/4 vol.). (5) Cooling the mixture to −5°-0° C. and stirring for a minimum of 12 hours. (6) Filtering the resulting solids. (7) Washing the solids with 0° C. isopropanol (6.8 L/1 vol). (8) Washing the solids with ethyl acetate (2×6.8 L/2 vol.). (9) Oven driing the solids to a constant weight at 35° C. under vacuum.

TABLE 7

| Crude (g) | Yield (g) | HPLC |
|---|---|---|
| 6816 g | 6435 g/94.4% | 99.8% |

Examples 27-45

Examples 27-45, below, reflect exemplary processes and methods relating to solvent system selected for the formation or separation of polymorphs Form A and Form B.

TABLE 8

Characterization summary for Viloxazine HCl Crystalline Forms A and B

| Form | Conditions | XRPD | DSC Peaks (° C.) | TGA Wt. Loss (wt %) | 1H NMR | API to HCl ratio | Moisture Sorption (wt % at 90% RH) |
|---|---|---|---|---|---|---|---|
| A (anhydrate) | binary-solvent with MeCN as anti-solvent (fast and slow cooling) | Crystalline | 188 | 0.0 | consistent w/ structure | 1:0.9 | Non-hygroscopic, 0.25 wt % |
| B (anhydrate) | Slurry in water, 9:1 MeCN/H2O and 9:1 acetone/H2O; most binary-solvent with MTBE and toluene as anti-solvents | Crystalline | 186 | 0.0 | consistent w/ structure | 1:1 | Non-hygroscopic, 0.31 wt % |

Example 27

TABLE 9

Solvent Screen for Viloxazine HCl

| Solvent | Drug Amt (mg) | Solvent amount (mL) | Temp (° C.) | Soluble (Visual) | Gravimetric Solubility at RT (mg/mL) | ICH class | ICH limit (ppm) | b.p. (° C.) |
|---|---|---|---|---|---|---|---|---|
| water | 3.5 | 0.1 | RT | Yes | >35 | ~ | ~ | 100 |
| acetic acid | 3.1 | 0.1 | 55 | Yes | 6.7 | 3 | * | 115 |
| methanol | 3.2 | 0.1 | 55 | Yes | 16.0 | 2 | 3000 | 65 |
| ethanol | 3.6 | 0.8 | 55 | Yes | 1.9 | 3 | * | 78 |
| IPA | 3.8 | 1.6 | 55 | Yes | 0.3 | 3 | * | 82 |
| t-AmOH | 3.2 | 1.6 | 55 | No | 0.0 | ~ | ~ | 102 |
| 1-butanol | 3.4 | 1.6 | 55 | No | 0.0 | 3 | * | 118 |
| DMF | 2.9 | 0.4 | 55 | Yes | 0.6 | 2 | 880 | 153 |
| acetonitrile | 3.9 | 1.6 | 55 | No | 0.0 | 2 | 410 | 81 |
| MeOAc | 3.8 | 1.6 | 55 | No | 0.0 | 3 | * | 58 |
| EtOAc | 3.2 | 1.6 | 55 | No | 0.0 | 3 | * | 77 |
| IPAc | 2.7 | 1.6 | 55 | No | 0.0 | 3 | * | 89 |
| acetone | 3.6 | 1.6 | 55 | No | 0.0 | 3 | * | 56 |
| MEK | 3.7 | 1.6 | 55 | No | 0.0 | 3 | * | 80 |
| MIBK | 2.6 | 1.6 | 55 | No | 0.0 | 3 | * | 117 |
| MTBE | 3.2 | 1.6 | 55 | No | 0.0 | 3 | * | 56 |
| THF | 3.3 | 1.6 | 55 | No | 0.1 | 2 | 720 | 66 |
| 2-MeTHF | 2.6 | 1.6 | 55 | No | 0.0 | ~ | ~ | 79 |
| dioxane | 2.6 | 1.6 | 55 | No | 0.0 | 2 | 380 | 101 |
| toluene | 3.1 | 1.6 | 55 | No | 0.0 | 2 | 890 | 111 |
| xylene | 3.2 | 1.6 | 55 | No | 0.0 | 2 | 2170 | 140 |
| DCM | 2.5 | 4.8 | 40 | No | 0.0 | 2 | 600 | 40 |
| cyclohexane | 3.6 | 1.6 | 55 | No | 0.0 | 2 | 3880 | 81 |
| heptane | 3.5 | 1.6 | 55 | No | 0.0 | 3 | * | 98 |
| NMP | 3.1 | 0.4 | 55 | Yes | 4.9** | 2 | 530 | 202 |

Example 28

TABLE 10

Single Solvent Crystallizations of Viloxazine HCl Using a Fast Cooling Profile

| Drug amt (mg) | Solvent | Amount (mL) | Temp. (° C.) | Cooling | Precipitation | Recovery (mg) | Yield (%) | Form [XRPD] |
|---|---|---|---|---|---|---|---|---|
| 26.6 | AcOH | 0.30 | 75 | Fast | Yes | 11.1 | 41.7 | A |
| 25.3 | DMF | 1.00 | 75 | Fast | Yes | 18.4 | 72.7 | A |
| 25.9 | NMP | 1.05 | 75 | Fast | Yes | 16.0 | 61.8 | A |
| 28.8 | water | 0.20 | 75 | Fast | No/scr/evap | n/a | n/a | B |

Example 29

TABLE 11

Single Solvent Crystallizations of Viloxazine HCl Using a Slow Cooling Profile

| Drug amt (mg) | Solvent | Amount (mL) | Temp. (° C.) | Cooling | Precipitation | Recovery (mg) | Yield (%) | Form [XRPD] |
|---|---|---|---|---|---|---|---|---|
| 25.0 | MeOH | 0.5 | 60 | 20° C./h | Yes | 11.2 | 44.8 | A |
| 24.3 | AcOH | 0.3 | 75 | 20° C./h | No/scr/ppt | 11.0 | 45.3 | A |
| 24.2 | NMP | 1.0 | 75 | 20° C./h | Yes | 15.1 | 62.4 | A |
| 29.3 | water | 0.2 | 75 | 20° C./h | No/scr/evap | n/a | n/a | B |

Example 30

TABLE 12

Binary Solvent Crystallizations of Viloxazine HCl Using MEOH as a Primary Solvent and a Fast Cooling Profile

| Drug amt (mg) | MeOH (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 25.2 | 0.5 | MeCN | 2.00 | 60 | Fast | some ppt* | Yes | 13.0 | 51.6 | A |
| 24.8 | 0.5 | EtOAc | 2.00 | 60 | Fast | turbid | Yes | 19.8 | 79.8 | B |
| 26.1 | 0.5 | acetone | 2.00 | 60/50 | Fast | turbid* | Yes | 19.3 | 73.9 | A |
| 25.5 | 0.5 | MTBE | 0.85 | 60/50 | Fast | ppt | Yes | 20.7 | 81.2 | B |
| 24.7 | 0.5 | toluene | 2.00 | 60 | Fast | turbid* | Yes | 18.2 | 73.7 | B |

Example 31

TABLE 13

Binary Solvent Crystallizations of Viloxazine HCl Using MEOH as a Primary Solvent and a Slow Cooling Profile

| Drug amt (mg) | MeOH (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 25.6 | 0.5 | MeCN | 6.00 | 60 | 20° C./h | some ppt* | Yes | 14.4 | 56.3 | A |
| 24.5 | 0.5 | acetone | 2.00 | 60/50 | 20° C./h | turbid | Yes | 17.9 | 73.1 | A |
| 25.6 | 0.5 | MTBE | 0.87 | 60/50 | 20° C./h | ppt | Yes | 19.5 | 76.2 | B |
| 25.2 | 0.5 | THF | 3.00 | 60 | 20° C./h | turbid | Yes | 19.8 | 78.6 | A |
| 24.4 | 0.5 | toluene | 2.00 | 60 | 20° C./h | light turbid | Yes | 16.6 | 68.0 | B |
| 25.7 | 0.5 | heptane | 1.00 | 60 | 20° C./h | 2 layers | Yes | 16.8 | 65.4 | A |

Example 32

TABLE 14

Binary Solvent Crystallizations of Viloxazine HCl Using EtOH as a Primary Solvent and a fast Cooling Profile

| Drug amt (mg) | EtOH (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 25.9 | 1.5 | MeCN | 6.00 | 75 | Fast | clear | Yes | 11.2 | 43.2 | A |
| 25.2 | 1.5 | MTBE | 3.00 | 75/50 | Fast | turbid | Yes | 20.1 | 79.8 | B |
| 24.7 | 1.5 | toluene | 6.00 | 75 | Fast | clear | Yes | 19.1 | 77.3 | B |
| 24.6 | 1.5 | heptane | 5.00 | 75 | Fast | turbid | Yes | 20.2 | 82.1 | B |

Example 33

TABLE 15

Binary Solvent Crystallizations of Viloxazine HCl Using EtOH as a Primary Solvent and a Slow Cooling Profile

| Drug amt (mg) | EtOH (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 25.5 | 1.5 | MeCN | 6.00 | 75 | 20° C./h | clear | No/scr/ppt | 6.2 | 24.3 | A |
| 25.6 | 1.5 | EtOAc | 6.00 | 75 | 20° C./h | clear | Yes | 19.3 | 75.4 | A |
| 25.2 | 1.5 | acetone | 6.00 | 75/50 | 20° C./h | clear | Yes | 16.3 | 64.7 | A |
| 25.6 | 1.5 | MTBE | 2.55 | 75/50 | 20° C./h | turbid | Yes | 21.1 | 82.4 | B |
| 26.2 | 1.5 | toluene | 6.00 | 75 | 20° C./h | clear | No/scr/ppt | 7.7 | 29.4 | B |

Example 34

TABLE 16

Binary Solvent Crystallizations of Viloxazine HCl Using Acetic Acid as a Primary Solvent and a Fast Cooling Profile

| Drug amt (mg) | AcOH (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 25.2 | 0.3 | MeCN | 7.00 | 75 | Fast | clear | Yes | 14.6 | 57.9 | A |
| 25.3 | 0.3 | MTBE | 1.00 | 75/50 | Fast | turbid | Yes | 19.5 | 77.1 | B |
| 25.8 | 0.3 | toluene | 7.00 | 75 | Fast | clear | Yes | 19.9 | 77.1 | B |
| 24.7 | 0.3 | DCM | 7.00 | 75/40 | Fast | clear | No/scr/evap | n/a | n/a | A |

Example 35

TABLE 17

Binary Solvent Crystallizations of Viloxazine HCl Using Acetic Acid as a Primary Solvent and a Slow Cooling Profile

| Drug amt (mg) | AcOH (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 25.4 | 0.3 | MeCN | 7.00 | 75 | 20° C./h | clear | No/scr/ppt | 11.3 | 44.5 | A |
| 25.8 | 0.3 | EtOAc | 2.40 | 75 | 20° C./h | turbid | Yes | 18.9 | 73.3 | A |
| 25.5 | 0.3 | acetone | 1.75 | 75/50 | 20° C./h | turbid | Yes | 17 | 66.7 | B |
| 25.6 | 0.3 | MTBE | 0.80 | 75/50 | 20° C./h | turbid | Yes | 16.6 | 64.8 | B |

TABLE 17-continued

Binary Solvent Crystallizations of Viloxazine HCl Using Acetic Acid as a Primary Solvent and a Slow Cooling Profile

| Drug amt (mg) | AcOH (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 25 | 0.3 | THF | 1.25 | 75/60 | 20° C./h | turbid | Yes | 17.8 | 71.2 | B |
| 25.1 | 0.3 | toluene | 7.00 | 75 | 20° C./h | clear | Yes | 18.1 | 72.1 | B |
| 25.8 | 0.3 | DCM | 7.00 | 75/40 | 20° C./h | clear | No/scr/evap | n/a | n/a | A |

Example 36

TABLE 18

Binary Solvent Crystallizations of Viloxazine HCl Using DMF as a Primary Solvent and a Fast Cooling Profile

| Drug amt (mg) | DMF (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 25.1 | 1.0 | MeCN | 6.00 | 75 | Fast | clear | Yes | 17.8 | 70.9 | A |
| 26 | 1.0 | MTBE | 0.75 | 75/50 | Fast | turbid | Yes | 20.1 | 77.3 | B |
| 25.9 | 1.0 | THF | 2.00 | 75/60 | Fast | turbid | Yes | 19.7 | 76.1 | A |
| 25.2 | 1.0 | toluene | 3.00 | 75 | Fast | turbid | Yes | 20.1 | 79.8 | B |
| 24.7 | 1.0 | heptane | 1.00 | 75 | Fast | 2 layers | Yes | 18.6 | 75.3 | A |
| 25.2 | 1.0 | DCM | 6.00 | 75/40 | Fast | clear | Yes | 9.2 | 36.5 | A |

Example 37

TABLE 19

Binary Solvent Crystallizations of Viloxazine HCl Using DMF as a Primary Solvent and a Slow Cooling Profile

| Drug amt (mg) | DMF (mL) | Anti-Solvent | Amount (mL) | Temp. (° C.) | Cooling | Appearance after anti-solvent addition | Precipitaion | Recovery (mg) | Yield (%) | Form |
|---|---|---|---|---|---|---|---|---|---|---|
| 25.9 | 1.0 | MeCN | 6.00 | 75 | 20° C./h | clear | Yes | 15.4 | 59.5 | A |
| 26.1 | 1.0 | EtOAc | 1.90 | 75 | 20° C./h | turbid | Yes | 20.2 | 77.4 | A |
| 25.8 | 1.0 | MTBE | 0.85 | 75/50 | 20° C./h | turbid | Yes | 19.3 | 74.8 | A |
| 26.1 | 1.0 | THF | 2.25 | 75/60 | 20° C./h | turbid | Yes | 20.2 | 77.4 | A |
| 25.0 | 1.0 | toluene | 3.00 | 75 | 20° C./h | turbid | Yes | 20.7 | 82.8 | B |
| 25.6 | 1.0 | heptane | 1.00 | 75 | 20° C./h | 2 layers | Yes | 18.3 | 71.5 | A |
| 25.0 | 1.0 | DCM | 6.00 | 75/40 | 20° C./h | clear | No/scr/ev/ppt | 12.8 | 51.2 | A |

Example 38

TABLE 20

Binary Solvent Crystallizations of Viloxazine HCl Using NMP as a Primary Solvent and a Fast Cooling Profile

| Drug amt (mg) | NMP (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 25.7 | 1.0 | MeCN | 6.00 | 75 | Fast | clear | Yes | 14.1 | 54.9 | A |
| 26.2 | 1.0 | EtOAc | 2.00 | 75 | Fast | Turbid | Yes | 19.6 | 74.8 | A |
| 25.6 | 1.0 | acetone | 2.00 | 75/50 | Fast | Turbid | Yes | 19.0 | 74.2 | A |
| 25.6 | 1.0 | THF | 2.90 | 75/60 | Fast | Turbid | Yes | 19.4 | 75.8 | A |
| 25.8 | 1.0 | toluene | 3.00 | 75 | Fast | Turbid | Yes | 20.2 | 78.3 | B |

TABLE 20-continued

Binary Solvent Crystallizations of Viloxazine HCl Using NMP as a Primary Solvent and a Fast Cooling Profile

| Drug amt (mg) | NMP (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 25.4 | 1.0 | heptane | 1.00 | 75 | Fast | 2 layers | Yes | 18.4 | 72.4 | A |
| 25.6 | 1.0 | DCM | 6.00 | 75/40 | Fast | clear | small | 1.7 | 6.6 | A |

Example 39

TABLE 21

Binary Solvent Crystallizations of Viloxazine HCl Using NMP as a Primary Solvent and a Slow Cooling Profile

| Drug amt (mg) | NMP (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 25.8 | 1.0 | MeCN | 6.00 | 75 | 20° C./h | clear | No/scr/ppt | 12.1 | 46.9 | A |
| 24.9 | 1.0 | EtOAc | 2.00 | 75 | 20° C./h | Turbid | Yes | 18.1 | 72.7 | A |
| 25.8 | 1.0 | acetone | 2.55 | 75/50 | 20° C./h | Turbid | Yes | 18.5 | 71.7 | A |
| 24.7 | 1.0 | MTBE | 1.30 | 75/50 | 20° C./h | Turbid | Yes | 19.3 | 78.1 | B |
| 25.7 | 1.0 | THF | 2.90 | 75/60 | 20° C./h | Turbid | Yes | 19.6 | 76.3 | A |
| 25.7 | 1.0 | toluene | 3.25 | 75 | 20° C./h | Turbid | Yes | 20.4 | 79.4 | B |
| 25.2 | 1.0 | heptane | 1.00 | 75 | 20° C./h | 2 layers | Yes | 17.6 | 69.8 | A |
| 25.6 | 1.0 | DCM | 6.00 | 75/40 | 20° C./h | clear | No/scr/ev/ppt | 12.6 | 49.2 | A |

Example 40

TABLE 22

Binary Solvent Crystallizations of Viloxazine HCl Using Water as a Primary Solvent and a Fast Cooling Profile

| Drug amt (mg) | Water (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 25.5 | 0.2 | MeOH | 5.00 | 75/60 | Fast | Clear | No/scr/evap | n/a | n/a | B |
| 25.3 | 0.2 | EtOH | 5.00 | 75 | Fast | Clear | No/scr/evap | n/a | n/a | A |
| 25.2 | 0.2 | IPA | 5.00 | 75 | Fast | Clear | No/scr/ppt | 8.6 | 34.1 | A |
| 26 | 0.2 | acetone | 5.00 | 75/50 | Fast | Clear | Yes | 18.3 | 70.4 | A |
| 24.9 | 0.2 | MeCN | 5.00 | 75 | Fast | Clear | Yes | 10.8 | 43.4 | A |
| 25.2 | 0.2 | DMF | 5.00 | 75 | Fast | Clear | No/scr/ev/ppt | 11.9 | 47.2 | A |
| 25.9 | 0.2 | NMP | 5.00 | 75 | Fast | Clear | No/scr/evap | n/a | n/a | n/a |

Example 41

TABLE 23

Binary Solvent Crystallizations of Viloxazine HCl Using Water as a Primary Solvent and a Slow Cooling Profile

| Drug amt (mg) | Water (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 26 | 0.2 | MeOH | 5.00 | 75/60 | 20° C./h | clear | No/scr/evap | n/a | n/a | B |
| 25.0 | 0.2 | IPA | 5.00 | 75 | 20° C./h | clear | Yes | 8.6 | 34.4 | A |
| 25.0 | 0.2 | acetone | 5.00 | 75/50 | 20° C./h | clear | Yes | 13.3 | 53.2 | A |
| 25.1 | 0.2 | THF | 5.00 | 75/60 | 20° C./h | clear | Yes | 13.9 | 55.4 | A |
| 25.2 | 0.2 | dioxane | 5.00 | 75 | 20° C./h | clear | Yes | 17.4 | 69.0 | A |
| 25.4 | 0.2 | MeCN | 5.00 | 75 | 20° C./h | clear | No/scr/ppt | 8.3 | 32.7 | A |

TABLE 23-continued

Binary Solvent Crystallizations of Viloxazine HCl Using Water as a Primary Solvent and a Slow Cooling Profile

| Drug amt (mg) | Water (mL) | Anti-Solvent | Amount (mL) | Temp. (° C.) | Cooling | Appearance after anti-solvent addition | Precipitation | Recovery (mg) | Yield (%) | Form |
|---|---|---|---|---|---|---|---|---|---|---|
| 25.9 | 0.2 | DMF | 5.00 | 75 | 20° C./h | clear | No/scr/ev/ppt | 14.1 | 54.4 | A |
| 25.3 | 0.2 | NMP | 5.00 | 75 | 20° C./h | clear | No/scr/evap | n/a | n/a | n/a |

Example 42

TABLE 24

Scale-Up Experiments of Form A and Form B

| Drug amt (mg) | MeOH (mL) | Anti-Solvent | Amount (mL) | Temp. (° C.) | Cooling | Appearance after anti-solvent addition | Precipitation | Recovery (mg) | Yield (%) | Form [XRPD] |
|---|---|---|---|---|---|---|---|---|---|---|
| 500 | 10 | acetone | 40 | 60/50 | 20° C./h | Clear | Yes | 401.5 | 80.3 | A+ |
| 500 | 10 | MTBE | 15 | 60/50 | Fast | Turbid | Yes | 436.9 | 87.4 | B |
| 500 | 10 | MeCN | 60 | 60 | Fast | Clear | Yes | 285.5 | 57.1 | A |

Example 43

TABLE 25

Stability Evaluation of viloxazine HCl polymorphs.

| Starting Form | Amount (mg) | Solvent | Amount (mL) | Temp (° C.) | Form in 7 days | Form in 14 days |
|---|---|---|---|---|---|---|
| A + B | 30.6 | MeOH | 0.5 | RT | A + B | A + B |
| | 30.0 | EtOH | 0.5 | RT | A + B | A + B |
| | 30.5 | IPA | 0.5 | RT | A + B | A + B |
| | 29.9 | THF | 0.5 | RT | A + B | A + B |
| | 31.3 | AcOH | 0.5 | RT | A + B | A + B |
| | 31.7 | DMF | 0.5 | RT | A + B | A + B |
| | 30.2 | NMP | 0.5 | RT | A + B | A + B |
| | 41.5 | water | 0.5 | RT | B | B |
| A | 16.3 | MeCN | 0.4 | RT | A | A |
| | 18.7 | MeOH | 0.4 | RT | A | A |
| | 25.8 | water | 0.4 | RT | A | A |
| B | 15.1 | MeCN | 0.4 | RT | B | B |
| | 16.7 | MeOH | 0.4 | RT | B | B |
| | 31.7 | water | 0.4 | RT | B | B |

Example 44

TABLE 26

Stability Evaluation of viloxazine HCl polymorphs.

| Form A+ (mg) | Form B (mg) | Solvent | Amount (mL) | Temp. (° C.) | Form in 6 days | Form in 12 days |
|---|---|---|---|---|---|---|
| 14.6 | 14.7 | toluene | 0.5 | RT | A + B* | A + B* |
| 14.7 | 14.6 | MeCN | 0.5 | RT | A + B* | B+** |
| 14.9 | 14.6 | acetone | 0.5 | RT | A + B* | A + B* |
| 14.9 | 14.7 | MeCN/10% water | 0.5 | RT | B | B |
| 15.4 | 15.5 | acetone/10% water | 0.5 | RT | B | B |
| 16.0 | 15.6 | toluene | 0.5 | 40 | A + B* | A + B* |
| 16.4 | 16.3 | MeCN | 0.5 | 40 | A + B* | B+** |
| 15.7 | 15.8 | acetone | 0.5 | 40 | A + B* | A + B* |
| 20.9 | 19.9 | MeOH | 0.5 | 40 | A + B | A + B |

Example 45

TABLE 27

Gravimetric Solubility of Viloxazine HCl Form A and Form B

| Starting Form | API amount (mg) | Solvent | Solvent amount (mL) | Temp (° C.) | Solubility (mg/mL) | Final Form |
|---|---|---|---|---|---|---|
| Form A | 31.5 | water | 0.3 | RT | 43.54 | A |
| | 17.7 | methanol | 0.3 | RT | 10.90 | A |
| Form B | 29.4 | water | 0.3 | RT | 41.89 | B |
| | 23.0 | methanol | 0.3 | RT | 10.73 | B |

TABLE 28

Thermal Stability Study at 60° C.

| Starting Form | Form after 8 days | Form after 14 days |
|---|---|---|
| A | A | A |
| B | B | B |

TABLE 28-continued

Thermal Stability Study at 60° C.

| Starting Form | Form after 8 days | Form after 14 days |
|---|---|---|
| A + B | A + B | A + B |
| A + B | A + B | A + B |

TABLE 29

Thermal Stress Experiments on Viloxazine HCl Using DSC method

| Starting Form | DSC method | Final Form [XRPD] |
|---|---|---|
| A | 30-170° C.(10° C./min), hold 170° C./30 min | A |
| B | 30-170° C.(10° C./min), hold 170° C./30 min | B |
| A + B | 30-170° C.(10° C./min), hold 170° C./30 min | A + B |
| A + B | 30-170° C.(10° C./min), hold 170° C./180 min | A + B |
| B | 30-170° C.(10° C./min), hold 170° C./180 min | B |
| A | 30-170° C.(10° C./min), hold 170° C./180 min | A |

TABLE 30

DSC Experiments on Viloxazine HCl with various ramping rates

| | Heating rate | | | | | |
|---|---|---|---|---|---|---|
| | 1° C./min | | 10° C./min | | 50° C./min | |
| Form | Peak (° C.) | Heat of fusion (J/g) | Peak (° C.) | Heat of fusion (J/g) | Peak (° C.) | Heat of fusion (J/g) |
| A | 187.0 | 199.3 | 188.4 | 204.6 | 188.6 | 203.6 |
| B | 185.6 | 202.2 | 186.5 | 202.0 | 187.3 | 205.4 |
| A + B | 186.5 | 196.4 | 186.9 | 194.6 | 189.3 | 189.4 |

TABLE 31

Humidity Chamber Study on Viloxazine HCl at 95% RH

| Starting Form | Amount (mg) | Form in 7 days |
|---|---|---|
| A | 8.4 | A |
| B | 7.2 | B |
| A + B | 14.5 | A + B |

While this description is made with reference to exemplary embodiments, it will be understood by those skilled in the art that various changes may be made and equivalents may be substituted for elements thereof without departing from the scope. In addition, many modifications may be made to adapt a particular situation or material to the teachings hereof without departing from the essential scope. Also, in the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

The invention claimed is:

1. A method of manufacturing N-benzyl viloxazine or a pharmaceutically acceptable salt thereof, the method comprising:

(a) reacting a compound of formula

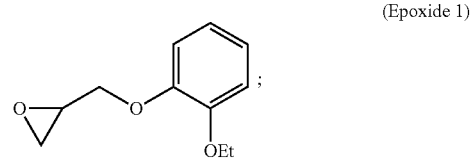 [SMILES: CCOc1ccccc1OCC1CO1]

(Epoxide 1)

with N-benzyl-aminoethanol to form a diol compound of formula

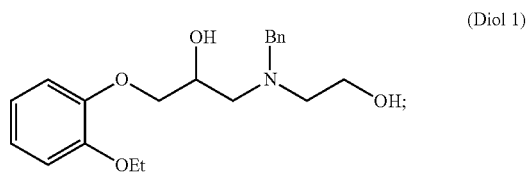 [SMILES: CCOc1ccccc1OCC(O)CN(CCO)Cc1ccccc1]

(Diol 1)

(b) contacting the diol compound in a solvent system with a base to generate a basic system; and, (c) contacting the basic system with a cyclization agent to produce N-benzyl viloxazine having the following formula:

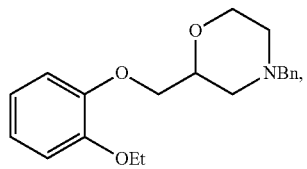

wherein Et is an ethyl group and Bn is a benzyl group.

2. The method according to claim 1, wherein a phase transfer catalyst is utilized in step (c).

3. The method according to claim 2, wherein the phase transfer catalyst is benzyltriethylammonium chloride.

4. The method according to claim 1, wherein the solvent system is a liquid-liquid biphasic system or a monophasic liquid system.

5. The method according to claim 4, wherein the solvent system is a liquid-liquid biphasic system.

6. The method according to claim 5, wherein the liquid-liquid biphasic system comprises water.

7. The method according to claim 4, wherein the solvent system is a monophasic liquid system.

8. The method according to claim 7, wherein the monophasic liquid system comprises toluene.

9. The method according to claim 1, wherein the base is a solid.

10. The method according to claim 9, wherein the base is sodium hydroxide.

11. The method according to claim 1, wherein the cyclization agent is a sulfonyl halide selected from the group consisting of tosyl chloride, brosyl chloride, nosyl chloride, and mesyl chloride.

12. The method according to claim 1, wherein the cyclization agent is toluenesulfonyl chloride and the solvent system is a liquid-liquid biphasic system.

* * * * *